(12) United States Patent
Templier et al.

(10) Patent No.: US 10,955,315 B2
(45) Date of Patent: Mar. 23, 2021

(54) METHOD, DEVICE AND SYSTEM FOR MANIPULATING PORTIONS OF A RIGID BODY

(71) Applicant: ETH Zurich, Zurich (CH)

(72) Inventors: Thomas Templier, Zurich (CH); Richard Hahnloser, Zurich (CH)

(73) Assignee: ETH ZURICH, Zurich (CH)

( * ) Notice: Subject to any disclaimer, the term of this patent is extended or adjusted under 35 U.S.C. 154(b) by 281 days.

(21) Appl. No.: 15/776,791

(22) PCT Filed: Nov. 17, 2016

(86) PCT No.: PCT/EP2016/078059
§ 371 (c)(1),
(2) Date: May 17, 2018

(87) PCT Pub. No.: WO2017/085213
PCT Pub. Date: May 26, 2017

(65) Prior Publication Data
US 2018/0372593 A1 Dec. 27, 2018

(30) Foreign Application Priority Data

Nov. 17, 2015 (EP) ..................................... 15194866

(51) Int. Cl.
*B26D 7/32* (2006.01)
*G01N 1/08* (2006.01)
(Continued)

(52) U.S. Cl.
CPC ................. *G01N 1/08* (2013.01); *B26D 7/32* (2013.01); *G01N 1/06* (2013.01); *G01N 1/286* (2013.01);
(Continued)

(58) Field of Classification Search
CPC ........... B26D 7/32; B03C 1/02; B03C 1/0335; B03C 1/30; H01F 7/206
See application file for complete search history.

(56) References Cited

U.S. PATENT DOCUMENTS 5,915,323 A 6/1999 Len-Rios
10,040,062 B2 * 8/2018 Beebe ................. B01L 3/50825
(Continued)

FOREIGN PATENT DOCUMENTS

EP 0589636 3/1994
JP 2007033312 2/2007
(Continued)

*Primary Examiner* — Justin N Olamit
(74) *Attorney, Agent, or Firm* — JMB Davis Ben-David

(57) ABSTRACT

The invention relates to a method, a device, and a system for manipulating portions of a rigid body (1), and a computer program for the execution of the steps of the method for manipulating portions (20) of a rigid body (1). The method comprises the steps of providing a rigid body (1) comprising ultrathin-sectionable material, cutting an ultrathin portion (20) from the rigid body (1), providing the portion (20) at the surface of a liquid, providing at least one magnetic device (4), which produces a magnetic field or which is able to produce a magnetic field, using the magnetic field in order to provide a magnetic force, and using the magnetic force to move the portion (20) at the surface of the liquid. The device, the system and the computer program are adapted to carry out the method for manipulating portions (20) of a rigid body (1).

10 Claims, 17 Drawing Sheets

(51) Int. Cl.
   *G01N 1/06* (2006.01)
   *G01N 1/28* (2006.01)
   *G01N 33/483* (2006.01)

(52) U.S. Cl.
   CPC ... *G01N 33/483* (2013.01); *G01N 2001/2873* (2013.01)

(56) References Cited

U.S. PATENT DOCUMENTS

| | | |
|---|---|---|
| 2014/0045210 A1 | 2/2014 | Menges et al. |
| 2014/0099658 A1 | 4/2014 | Tuunanen |
| 2015/0344241 A1* | 12/2015 | Lykov .................... B65G 51/01 405/3 |

FOREIGN PATENT DOCUMENTS

| | | |
|---|---|---|
| WO | WO2014076350 | 5/2014 |
| WO | WO2015121533 | 8/2015 |

* cited by examiner

METHOD, DEVICE AND SYSTEM FOR MANIPULATING PORTIONS OF A RIGID BODY

CROSS-REFERENCE TO RELATED APPLICATIONS

This is the U.S. National Stage of International Patent Application No. PCT/EP2016/078059 filed on Nov. 17, 2016, which was published in English under PCT Article 21(2), and which in turn claims the priority of European Patent Application No. 15194866.8 filed Nov. 17, 2015.

FIELD OF THE INVENTION

In Connectomics, a field of neuroscience, which is concerned with mapping the connections of individual neurons in brain tissue, it is necessary to produce a large number of consecutive microscopic images of brain tissue samples in a volumetric fashion with a voxel resolution smaller than 50 nm×50 nm×50 nm. A rigid body of tissue cannot be imaged in depth because of photon and electron scattering. Therefore it is necessary to abrade the rigid body, for instance by producing series of ultrathin sections.

PRIOR ART AND TECHNICAL PROBLEM

Cutting and collecting ultrathin sections is routinely performed manually. In a typical procedure, a tissue sample is embedded in an embedding material, resulting in a rigid body. Portions, particularly tissue sections, of about 10 to 500 nanometers thickness are cut from the rigid body by a diamond knife, which is positioned close to the surface of a liquid contained in a reservoir. Directly after cutting, a newly produced portion becomes afloat at the surface of the liquid. During consecutive cutting cycles, floating portions, which sometimes adhere to each other, are produced at the surface of the liquid.

Portions or chains of portions are then removed from the reservoir by manually inserting a support structure, particularly an imaging grid, a microscope slide, or a silicon wafer, into the reservoir and fishing the sections by lifting the support structure. Alternatively, tissue sections are manually manipulated using a small structure such as an eyelid. Samples are then dried, further processed and subjected to electron microscopy or light microscopy.

Manual handling of ultrathin portions is technically challenging. Even if performed by highly experienced operators, the procedure is inefficient, because a large number of portions is lost or damaged during the fishing process. Furthermore, the method is too slow to produce a large number of portions in a reasonable time frame. However, in the field of Connectomics, it is crucial to acquire volumetric imagery of a tissue and collect large numbers of samples.

Consequently, a number of attempts to automate or improve different steps in the production of portions and the preparation of samples for microscopy have been made.

Hayworth and colleagues developed a device that automatically collects ultrathin portions produced by commercially available ultramicrotomes (ATUM/ATUMtome, U.S. Pat. No. 7,677,289 B2). The device comprises a tape rolling and unrolling system combined with a conveyer belt placed in a reservoir of a commercially available ultramicrotome. Portions are automatically produced by the ultramicrotome and automatically collected onto a moving tape on the conveyer belt. The conductive tape that carries portions is rolled into a reel during the portion collection process. In this manner, hundreds to thousands of portions can be collected without human interaction. The surface of the liquid contained in the reservoir is maintained at the same level during the process to ensure proper sectioning at the edge of the cutting device.

At the end of a cutting session, the reel is removed and the tape can be unrolled for further processing. Typically, a skilled experimenter cuts short stripes of tape approximately 8 cm long and sticks them onto a conductive substrate such as a silicon wafer. Around 15 stripes can be placed onto a 4-inch silicon wafer resulting in about up to 200 sections per silicon wafer. The conductive substrate can then be placed under a light microscope or into an imaging chamber of a scanning electron microscope and the portions of interest can be imaged.

Micheva and coworkers (Micheva et al., *Cold Spring Harb Protoc.* 2010(11)) described a semi-manual technique, in which a support structure is inserted obliquely into the reservoir of a commercial ultramicrotome before starting the cutting process. A chain of consecutive portions is then produced, manually detached from the edge of the cutting device with an eyelash, and slowly moved to the emerged part of the support structure. After anchoring one or two chains, the substrate is slowly withdrawn manually. This provides a flat support structure containing one or two chains of around 60 consecutive portions each. The portions can further be subjected to several cycles of immunohistochemistry and light microscopic imaging. Finally, the portions can be imaged with a scanning electron microscope.

The approach of Horstmann and colleagues (Horstmann et al., *PLoS ONE* 7(4): e35172, 2012) is similar to the one published by Micheva et al. Therein, the support structure is held by a manual manipulator anchored to a custom built holder. This allows the operator to retract the support structure gently after one or more chains of portions have been produced.

None of the described methods from the prior art are fully automated. For instance, the ATUM technique requires an operator to manually cut stripes from a conveyor belt and transfer them to support structures for microscopic imaging.

However, a full automation of the process would be advantageous to handle the large sample sizes, which are required particularly for Connectomics applications, in a reasonable time frame.

The problem to be solved by the present invention is to provide a method, a device and a system for manipulating portions of a rigid body in an easily manageable, easy to produce, cost efficient, time efficient, safe, and non-destructive manner.

This problem is solved by the subject matter of the method, the device, the system, and the computer program described herein.

Terms and Definitions

In the context of the present specification, the term sectionable material refers to a material, which is adapted to be divided, particularly cut, into thin sections, particularly of a thickness of 1 to 100000 nanometers, more particularly 5 to 20000 nanometers, most particularly 5 to 500 nanometers.

In the context of the present invention, the term ultrathin-sectionable material refers to a material, wherein a rigid body of said material is adapted to be divided, particularly cut, into thin sections, wherein the smallest Cartesian dimension of a section is at least 100 times, particularly at least 1000 times, more particularly at least 10000 times, smaller than the other two Cartesian dimensions of the section, wherein particularly the section has a thickness of 1 nm to 1000 nm or 1 nm to 100000 nm, more particularly 5 nm to 20000 nm, most particularly 5 nm to 500 nm.

In particular, the smallest Cartesian dimension of the section is at least 100 times, more particularly at least 1000 times, most particularly at least 10000 times, smaller than any of the three Cartesian dimensions of the rigid body.

In the context of the present invention, the term ultrathin portion refers to a portion, which is produced, particularly cut, from a rigid body of ultrathin-sectionable material, wherein the smallest Cartesian dimension of the portion is at least 100 times, particularly at least 1000 times, more particularly at least 10000 times, smaller than the other two Cartesian dimensions of the portion, wherein particularly the portion has a thickness of 1 nm to 1000 nm or 1 nm to 100000 nm, more particularly 5 nm to 20000 nm, most particularly 5 nm to 500 nm.

In particular, the smallest Cartesian dimension of the portion is at least 100 times, more particularly at least 1000 times, most particularly at least 10000 times, smaller than any of the three Cartesian dimensions of the rigid body.

In the context of the present specification, the term biological material particularly refers to an isolated component of an animal body, an isolated component of a plant body, or an isolated component of a human body, particularly an isolated component comprising a tissue, more particularly an animal tissue, a plant tissue, or a human tissue, most particularly a brain tissue, an organ or a part thereof, cells, particularly eukaryotic cells, more particularly human cells, or animal cells, or plant cells, prokaryotic cells, more particularly bacterial cells or archaeal cells, or parts thereof, viruses or bacteriophages or parts thereof, organelles or parts thereof, lipid membranes or parts thereof, biomolecules, or polymers of biomolecules or parts thereof.

In the context of the present invention, the term biological material preferably does not refer to an entire human body.

In the context of the present specification, the term biomolecule is used in its meaning known in the art of biology. It refers to proteins, polysaccharides, lipids, nucleic acids, particularly deoxyribonucleic acid (DNA) or ribonucleic acid (RNA).

In the context of the present specification, the term tissue is used in its meaning known in the art of biology and medicine. It refers to a part of an organism, particularly a human, an animal, or a plant comprising a plurality of cells. A tissue may further comprise an extracellular material, particularly an extracellular matrix.

In the context of the present specification, the term extracellular matrix is used in its meaning known in the art of cell biology. It refers to a biological material, which may be deposited outside of cells.

In the context of the present specification, the term magnetic device refers to a permanent magnet or an electromagnet or to an assembly of more than one permanent magnet or more than one electromagnet.

In the context of the present specification, the term magnetic material is used in its meaning known in the art of physics. It refers to a material having a magnetization in the absence of an external magnetic field.

In the context of the present specification, the term magnetizable material is used in its meaning known in the art of physics. It refers to a material, on which a magnetic force acts in the vicinity of an external magnetic field.

DESCRIPTION OF THE INVENTION

According to a first aspect of the invention, a method for manipulating at least one portion of a rigid body is provided, wherein the method comprises the steps of providing a rigid body comprising ultrathin-sectionable material, cutting an ultrathin portion from the rigid body, providing the portion at a surface of a liquid, providing at least one magnetic device, which produces a magnetic field or which is able to produce a magnetic field, and using the magnetic field in order to provide a magnetic force, and using the magnetic force to move the portion at the surface of the liquid.

In certain embodiments, the portion of a rigid body is floating on the surface of the liquid, partially submerged in the liquid, or swimming near the surface of the liquid.

In certain embodiments, the liquid comprises water, or ethanol, or methanol, or acetone.

In certain embodiments, the rigid body comprises a biological material and/or the rigid body comprises an ultrathin-sectionable material, wherein the portion cut from the rigid body is an ultrathin portion. In certain embodiments, the ultrathin-sectionable material comprises a biological material, particularly a tissue.

In certain embodiments, the rigid body comprises a biological material, particularly a tissue.

In certain embodiments, the rigid body comprises an ultrathin-sectionable material, wherein an ultrathin portion is cut from the rigid body.

In certain embodiments, the smallest Cartesian dimension of the portion of a rigid body is at least 100 times, particularly at least 1000 times, more particularly at least 10000 times, smaller than the other two Cartesian dimensions of the portion.

In particular, the smallest Cartesian dimension of the portion is at least 100 times, more particularly at least 1000 times, most particularly at least 10000 times, smaller than any of the three Cartesian dimensions of the rigid body.

In certain embodiments, the portion cut from the rigid body has a thickness of 1 nm to 1000 nm.

In certain embodiments, the portion cut from the rigid body has a thickness of 1 nm to 100000 nm, particularly 5 nm to 20000 nm, more particularly 5 nm to 500 nm.

In certain embodiments, the rigid body is a tissue block, wherein the tissue block is cut into tissue sections, before moving the tissue sections at the surface of the liquid.

In certain embodiments, the portion cut from the rigid body is a tissue section.

In certain embodiments, the rigid body, particularly the tissue block, is cut into portions, particularly tissue sections, using a diamond knife, particularly adapted for ultramicrotomy, more particularly an oscillating diamond knife.

Advantageously, an oscillating diamond knife allows easier detachment of adjacent portions.

In certain embodiments, the ultrathin-sectionable material comprises biological material, or is biological material.

In certain embodiments, the ultrathin-sectionable material comprises biological material or is biological material.

In certain embodiments, the biological material comprises ultrathin-sectionable material or is ultrathin-sectionable material.

In certain embodiments, the rigid body comprises at least one marker particle, wherein the marker particle can be visualized by an imaging technique, particularly photography, electron microscopy, or light microscopy, more particularly fluorescence microscopy.

In certain embodiments, the minimal extension of the marker particle is between 2 nanometers and 5 micrometers, particularly between 5 nanometers and 1 micrometer.

In certain embodiments, the marker particle is fluorescent or comprises a fluorescent substance.

In certain embodiments, the portion of a rigid body comprises at least one segment of a marker particle, particularly a segment generated by cutting of the marker particle.

In certain embodiments, the magnetic force acting on a portion of a rigid body is used to move the portion to a specified position at the surface of the liquid contained in a reservoir, and/or in order to separate a first portion of a rigid body from a second portion of a rigid body, to which it adheres, and/or in order to separate a portion of a rigid body from an object, particularly a cutting device, more particularly a diamond knife, even more particularly adapted for ultramicrotomy, most particularly an oscillating diamond knife, or a structure comprised in the reservoir containing the liquid, particularly a wall of the reservoir.

Using a magnetic force to move portions of a rigid body is especially advantageous compared to manual handling, because the portions can be manipulated quickly, reproducibly and without inflicting damage to the portions. Therefore, the respective portions may be handled automatically.

In certain embodiments, the portion of a rigid body comprises a magnetic or magnetizable material, wherein the magnetic field acts on the magnetic or magnetizable material, such that the magnetic force acts directly, that is immediately, on the portion.

In certain embodiments, a magnetic or magnetizable material is distributed in the rigid body and/or the rigid body is mechanically connected to a body of magnetic or magnetizable material.

In this manner, it may be achieved that each individual portion cut from the rigid body comprises a sufficient amount of the magnetic or magnetizable material, so that a sufficient magnetic force acts on a portion of a rigid body, if a magnetic field is provided in the vicinity of the portion.

In certain embodiments, the magnetic device is moved to a specified position, wherein the magnetic device being at the specified position is able to provide a magnetic field in order to exert a magnetic force on a portion of a rigid body, and wherein the portion is positioned at the surface of the liquid by the magnetic force.

Advantageously, portions of a rigid body may be sorted to support structures positioned in the reservoir by moving a magnetic device.

In certain embodiments, the magnetic device is positioned near the surface of the liquid, particularly above the surface of the liquid.

In certain embodiments, the magnetic device is moved by an actuator, or by an array of actuators, such that the distance between the magnetic device and the surface of the liquid is changed, so that the magnetic field can be used at the surface of the liquid.

In particular, the magnetic field provided by the magnetic device will be stronger at a position below the magnetic device at the surface of the liquid contained in the reservoir if the magnetic device is moved closer to the surface by the actuator. Portions of a rigid body in the vicinity of the magnetic device will then be moved towards the position of the strongest local magnetic field.

In certain embodiments, the magnetic field provided by the magnetic device is controlled by providing an electric current through an electromagnet or an array of electromagnets, wherein the electromagnet or the array of electromagnets is positioned near the surface of the liquid, so that the magnetic field provided by the electromagnet or the array of electromagnets can be used at the surface of the liquid. Consequently, the magnetic field provided by the electromagnet or array of electromagnets will be strongest at positions below the activated electromagnets at the surface of the liquid, so that portions of a rigid body in the vicinity of the active electromagnets will be moved towards the position of the strongest local magnetic field.

In certain embodiments, a floatable device is provided, wherein the floatable device floats at the surface of the liquid, and wherein the floatable device comprises a magnetic or magnetizable material, and wherein according to a first alternative, the magnetic field acts on the floatable device, such that a magnetic force acts on the floatable device, such that the floatable device is moved by the magnetic force, and wherein the floatable device exerts a mechanical force on at least one portion of a rigid body, such that the portion of a rigid body is moved at the surface of the liquid. According to a second alternative, the magnetic field provided by the floatable device exerts a magnetic force on at least one portion of a rigid body, such that the portion is moved at the surface of the liquid.

In certain embodiments, according to the first alternative, the floatable device is provided as a floatable knife or a floatable separator, wherein the floatable knife particularly comprises a blade and is able to separate a portion of a rigid body from a chain comprising portions of a rigid body, when the floatable knife is moved by the magnetic force.

In certain embodiments, according to the second alternative, the floatable device is provided as a floatable magnetic barrier, particularly a movable floatable magnetic barrier. Particularly, the floatable magnetic barrier is moved by a mechanical force or by a magnetic force provided by the magnetic device.

In certain embodiments, the magnetic device comprises the floatable barrier.

As a result of the magnetic force provided by the magnetic barrier, at least one portion of a rigid body may be moved.

In certain embodiments, the floatable magnetic barrier encloses a partial surface of the liquid.

In certain embodiments, the floatable magnetic barrier is moved to accumulate a plurality of portions of a rigid body at a partial surface of the liquid.

In certain embodiments, according to the first and/or second alternative, the floatable device comprises a wire loop, particularly a closed wire loop, wherein the wire loop is floating at the surface of the liquid.

In certain embodiments, the wire loop exhibits a diameter of 0.005 to 1 mm, particularly 0.05 to 0.4 mm.

Advantageously, a thin wire loop is able to float at the surface of the liquid by means of surface tension. Furthermore, a thin wire loop minimizes overlap of portions of a rigid body, with the wire loop, particularly when the portions are positioned on a support structure.

In certain embodiments, the magnetic device comprises a wire loop.

Particularly, as a result of the magnetic force provided by the wire loop, at least one portion of a rigid body may be moved.

In certain embodiments, the wire loop encloses a partial surface of the liquid.

In certain embodiments, the wire loop is moved to accumulate a plurality of portions of a rigid body at a partial surface of the liquid.

In certain embodiments, a loop, particularly a closed loop, is provided at the surface of the liquid, wherein the loop is moved at the surface of the liquid in order to exert a mechanical force on at least one portion of a rigid body.

In certain embodiments, the loop exhibits a diameter of 0.005 to 1 mm, particularly 0.05 to 0.4 mm.

In certain embodiments, the loop encloses a partial surface of the liquid.

In certain embodiments, the loop is moved to accumulate a plurality of portions of a rigid body at a partial surface of the liquid.

In certain embodiments, a portion of a rigid body is moved at the surface of the liquid to a position above a support structure by using the magnetic force, and the distance between the surface of the liquid and the support structure is reduced, such that the portion of a rigid body is carried by the support structure.

In certain embodiments, the portion of a rigid body is carried by the support structure, such that the portion of a rigid body directly weighs on the support structure or such that the portion of a rigid body weighs on a liquid film comprising a liquid, wherein the liquid film is positioned on the support structure or on a part of the support structure.

In certain embodiments, the support structure comprises an imaging grid adapted for use in electron microscopy, particularly transmission electron microscopy (TEM), or a wafer, particularly a silicon wafer comprising a thin membrane, or a microscope slide for use in light microscopy.

Advantageously, the method disclosed herein may be used to accumulate a large number of portions of a rigid body at a high density above a support structure, so that a large number of samples may be imaged by a high-resolution imaging technique such as electron microscopy in a single experiment. The possibility of the method provided by the invention to position and to collect portions of a rigid body directly onto a support structure represents a major advantage over other methods from the prior art and is a prerequisite for full automation.

Advantageously, no post-processing such as manual cutting of conveyor belt stripes is necessary when applying the method provided by the invention. Compared to the ATUM technology, the density of portions of a rigid body on a support structure can be increased by at least a factor of 10, which represents a significant advantage particularly for high throughput image generation using for example multi-beam electron microscopes.

Furthermore, the high density of portions of a rigid body on support structures, which can be achieved by the method disclosed herein allows performing chemical treatments, such as staining, using small amounts of reagents and without any contamination.

A flat support structure, such as a silicon wafer, is particularly advantageous for use with multi beam scanning electron microscopes to allow an excellent focus of all electron beams simultaneously. Particularly, portions of a rigid body collected on silicon wafers may also be imaged by fluorescent microscopy, which has been so far unpractical with the ATUM technique due to auto-fluorescence of the conveyor belt copper tape.

In certain embodiments at least one image, particularly a high resolution image, is taken of a plurality of portions, wherein the order, in which the portions have been provided, is determined by means of the at least one image.

In certain embodiments, an optically detectable pattern, particularly a marking, is introduced into the rigid body, wherein at least a part of the pattern on a respective portion cut from the rigid body is detected by means of taking the at least one image, and wherein the order, in which the portions have been provided, is determined by means of the part of the pattern.

In certain embodiments, the pattern comprises at least one recess in the rigid body, wherein particularly the at least one recess is introduced into the rigid body by means of a laser beam.

In certain embodiments, the pattern comprises at least one plurality of parallel lines, particularly arranged at an angle with respect to a longitudinal axis of the rigid body. This results in a pattern of dots on at least one edge of portions cut from the rigid body, wherein the order, in which the portions have been cut from the rigid body can be determined by means of the pattern of dots, particularly at least one distance between pairs of dots.

In particular, a computer algorithm may be used to determine the order, in which the portions have been cut from the rigid body, from the optically detectable pattern.

In certain embodiments, the order, in which the portions have been cut from the rigid body, is determined by vision based tracking. In particular, this requires that the magnetic devices are not occluding the view of the surface of the liquid in the reservoir, for example the magnetic devices are transparent or placed below the reservoir or inside the reservoir. In particular, the vision based tracking can be performed by brightfield microscopy, or fluorescence microscopy imaging, and the order may be determined by means of a computer algorithm.

In certain embodiments the method comprises determining the order, in which the portions of a rigid body have been provided, wherein the method further comprises the steps of taking at least one image, particularly a high resolution image, of a plurality of portions of a rigid body, generating a data set for each portion of the at least one image, comparing each pair of data sets, wherein a distance value is determined for each pair of data sets, and wherein the distance value reflects the similarity or dissimilarity of the respective pair of data sets, wherein particularly the similarity value is the maximum of the cross-correlation function of two images, generating a plurality of orders of the data sets, determining the sum of distance values of neighboring pairs of data sets of the respective order, comparing the sums of distance values of the generated orders, and selecting the order having the maximal sum of distance values reflecting the similarity, or having the minimal sum of distance values reflecting the dissimilarity.

Therein, the determined order is essentially the order in which the portions of a rigid body have been provided, particularly cut from a rigid body comprising ultrathin-sectionable material.

Particularly, neighboring data sets stem from portions of a rigid body that have been cut successively by a cutting device, particularly a diamond knife, more particularly adapted for ultramicrotomy, most particularly an oscillating diamond knife.

In certain embodiments, an image displays at least one portion of a rigid body.

In certain embodiments, the data set for each portion of a rigid body of the at least one image comprises at least one value, particularly a physical value and/or a grey value and/or a color value.

In certain embodiments, the distance value is determined by a scale invariant feature transform (SIFT) algorithm. Therein, at least one feature of each data set is identified, a geometric transformation is determined for each pair of data sets, wherein by means of the geometric transformation features of the first data set are transformable into the features of the second data set of the pair, and the distance value of each pair of data sets is determined according to the geometric transformation.

In certain embodiments, an image is taken of a single portion of a rigid body, or of a group of portions of a rigid body.

In certain embodiments, an image is taken by photography, particularly digital photography.

In certain embodiments, a high resolution image is taken by combining a high resolution imaging technique, particularly light microscopy, more particularly bright field microscopy, dark field microscopy, phase contrast microscopy, differential interference contrast microscopy, stimulated emission depletion microscopy, stochastic optical reconstruction microscopy, photo activation localization microscopy or electron microscopy, more particularly scanning electron microscopy, electron tomography or transmission electron microscopy with photography, particularly digital photography.

In certain embodiments, images are taken of portions of a rigid body carried by a support structure, particularly wherein an imaging technique such as electron microscopy or light microscopy is used.

In certain embodiments, images are taken of portions of a rigid body floating at the surface of the liquid contained in the reservoir.

In certain embodiments, identifying neighboring data sets results in providing an ordered list comprising the generated data sets such that the sum of distance values reflecting the similarity exhibits a maximum, or the sum of distance values reflecting the dissimilarity exhibits a minimum.

In certain embodiments, a total distance value is calculated for each of the generated orders, wherein the total distance value of an order is the sum of the distance values of all consecutive pairs of data sets of the generated order. In other words, if $(a_3, a_2, a_5, a_1, a_4)$ is a given order of data sets where $a_1, a_2, a_3, a_4, a_5$ are data sets and $d(a, b)$ is the distance value of the pair of data sets a and b, then the total distance of the order is $d(a_3, a_2)+d(a_2, a_5)+d(a_5, a_1)+d(a_1, a_4)$, In certain embodiments, the total distance values of the generated orders, are compared, wherein the order having the maximal total distance value reflecting the similarity, or having the minimal total distance value reflecting the dissimilarity is selected.

Advantageously, the method described herein may be used to determine the order, in which portions of a rigid body have been cut from a rigid body. This allows the reconstruction of three-dimensional structures of the investigated ultrathin-sectionable material by combination of two-dimensional images of portions of a rigid body.

In certain embodiments, at least one marker particle, particularly fluorescent marker particle, is provided in the rigid body, wherein the marker particle can be visualized by an imaging technique, particularly photography, electron microscopy, or light microscopy, more particularly fluorescence microscopy, and wherein the portions of the rigid body comprise at least one segment of said marker particle, and wherein the order, in which the portions have been provided, is determined by inspection of at least one optically detectable parameter of said segment. In particular, the at least one optically detectable parameter may be a size or a shape of the segment or a position of the segment in the respective portion.

In certain embodiments, a fluorescent filament is included in the rigid body, wherein each portion cut from the rigid body comprises a fluorescent spot which can be tracked by means of fluorescence microscopy.

In certain embodiments, a fingerprint of a plurality of portions of the rigid body is captured immediately after cutting the portion from the rigid body. Therein, each fingerprint could be matched to each portion after the sections have been collected.

In certain embodiments, the fingerprint is generated by the material contained in each portion, wherein the fingerprint is different between neighboring portions.

In certain embodiments, the fingerprint may be an optical fingerprint, particularly a fluorescent signal stemming from a dispersion of fluorescent particles in the rigid body. In this case, a high resolution light microscope could be placed in close proximity of the cutting area.

In certain embodiments, the fingerprint may be a magnetic fingerprint, particularly an ultrathin Radio-frequency identification (RFID) tag.

According to a second aspect of the invention, a device for manipulating at least one portion of a rigid body is provided, wherein the device comprises a reservoir, which contains a liquid or which is adapted to contain a liquid for receiving at least one ultrathin portion of a rigid body at the surface of the liquid. Further, the device for manipulating at least one portion of a rigid body comprises at least one magnetic device, particularly a permanent magnet or an electromagnet, which is able to produce a magnetic field for providing a magnetic force such that one or a plurality of ultrathin portions of a rigid body can be moved at the surface of the liquid by the magnetic force.

In certain embodiments, the reservoir comprises a volume of less than 10 liters, particularly less than 1 liter, more particularly less than 100 ml.

In certain embodiments, the magnetic device is adapted to move an ultrathin portion of a rigid body to a position at the surface of a liquid at a position accuracy of less than 10 mm, particularly less than 5 mm, more particularly less than 1 mm.

In certain embodiments, the device for manipulating at least one portion of a rigid body comprises a cutting device, particularly a diamond knife, more particularly adapted for ultramicrotomy, most particularly an oscillating diamond knife, wherein the cutting device is adapted to cut a portion, particularly a section, from a body, particularly a rigid body, particularly comprising ultrathin-sectionable material.

In certain embodiments, the cutting device comprises an apparatus for automated operation of the cutting device.

In certain embodiments, the device for manipulating at least one portion of a rigid body comprises at least one moving device, particularly a manipulator arm, wherein the moving device is mechanically connected to the magnetic device, and wherein the moving device is adapted to move the magnetic device to a specified position with respect to the reservoir.

In certain embodiments, the device for manipulating at least one portion of a rigid body comprises a permanent magnet, which is mechanically connected to a manipulator arm, wherein the manipulator arm is adapted to move the permanent magnet near, particularly above the surface of the liquid, so that the magnetic field provided by the permanent magnet may be used to produce a magnetic force acting on the at least one portion at the surface of the liquid.

Permanent magnets advantageously allow an especially simple design of a device for manipulating at least one portion of a rigid body at low costs.

In certain embodiments, the device for manipulating at least one portion of a rigid body comprises at least one actuator, wherein the actuator is mechanically connected to the magnetic device, particularly a permanent magnet, wherein the magnetic device is positioned above the surface of said liquid, and wherein the actuator is adapted to move the magnetic device such that the distance between the magnetic device and the surface of the liquid is changeable. Herewith, a portion of a rigid body may be influenced by the magnetic field provided by the magnetic device and, thus, may be moved by the magnetic device.

In certain embodiments, the device for manipulating at least one portion of a rigid body comprises a plurality of actuators, particularly electric actuators, hydraulic actuators, or pneumatic actuators, wherein the actuators are positioned in an array, particularly a linear array or a two-dimensional array, wherein each of the actuators is mechanically connected to a respective magnetic device, particularly a permanent magnet. The respective magnetic device is positioned above the reservoir, wherein each actuator is adapted to move the magnetic device, to which it is connected, such that the distance between the magnetic device and the reservoir is changeable, particularly in a direction perpendicular to the surface of the liquid contained in the reservoir.

In certain embodiments, the distance between the respective magnetic device and the surface of the liquid is changeable when the reservoir contains the liquid.

An array of permanent magnets coupled to actuators advantageously allows a simultaneous manipulation of several portions of a rigid body at specific locations at the surface of a liquid contained in the reservoir.

In certain embodiments, the magnetic device comprises at least one floatable device, which is moveable at the surface of a liquid, wherein the floatable device comprises a magnetic or magnetizable material. Therefore, the floatable device can be moved by a magnetic force provided by a magnet, particularly a permanent magnet or an electromagnet, comprised in the magnetic device, such that at least one portion of a rigid body is movable as a result of a magnetic force provided by the floatable device or a mechanical force provided by the floatable device.

In certain embodiments, the magnetic device comprises a plurality of electromagnets or permanent magnets positioned in an array, wherein the respective electromagnet or permanent magnet is positioned above the reservoir, and wherein the device for manipulating at least one portion of a rigid body comprises a control device, wherein the control device is adapted to control an electric current through each electromagnet or to control the distance of each permanent magnet above the liquid, such that said magnetic field produced by the electromagnet or permanent magnet is controllable by the control device.

In certain embodiments, the floatable device comprises a floatable knife, wherein the floatable knife is able to separate a portion of a rigid body from a chain comprising portions of a rigid body, and/or from a diamond edge of a diamond knife, and/or from a wall of the reservoir, when the floatable knife is moved by the magnetic force.

Advantageously, this embodiment of the invention solves the technical problem of providing individual portions of a rigid body at the surface of a liquid contained in the reservoir.

In certain embodiments, the floatable device comprises a floatable magnetic barrier, particularly a movable floatable magnetic barrier. Particularly, the floatable magnetic barrier is movable by a mechanical force or by a magnetic force provided by the magnetic device.

In certain embodiments, the floatable device comprises a wire loop, particularly a closed wire loop, wherein the wire loop is floating at the surface of the liquid.

In certain embodiments, the wire loop exhibits a diameter of 0.005 to 1 mm, particularly 0.05 to 0.4 mm.

In certain embodiments, the magnetic device comprises a plurality of electromagnets positioned in an array, wherein the respective electromagnet is positioned above the reservoir, and wherein the device for manipulating at least one portion of a rigid body comprises a control device, wherein the control device is adapted to control an electric current through each electromagnet, such that the magnetic field produced by the electromagnet is controllable by the control device.

In certain embodiments, the magnetic device comprises a wire loop, particularly a closed wire loop, wherein the wire loop is floating at the surface of the liquid.

In certain embodiments, the wire loop exhibits a diameter of 0.005 to 1 mm, particularly 0.05 to 0.4 mm.

In certain embodiments, the control device is adapted to control an electric current through the electromagnet, such that the magnetic field produced by the electromagnet is controllable by the control device, particularly wherein the electromagnet may be switched on or off by switching the electric current on or off, or wherein the control device is adapted to change the electric current flowing through the electromagnet such that the flux density of the magnetic field produced by the electromagnet may be changed.

In certain embodiments, the control device is adapted to control a movement of a manipulator arm, and/or an actuator, and/or a camera for taking images of a portion of a rigid body, and/or a device for high resolution imaging, particularly a light microscope or an electron microscope.

Advantageously, the control device may further be adapted to control components of the device for manipulating at least one portion of a rigid body, which allows an automated operation of the device for manipulating at least one portion of a rigid body.

In certain embodiments, the device for manipulating at least one portion of a rigid body comprises a device for reducing the distance between the surface of the liquid and a support structure, wherein the device for reducing the distance particularly comprises a syringe pump, wherein the syringe pump is adapted to remove the liquid from the reservoir.

In certain embodiments, the device for reducing the distance between the surface of the liquid and the support structure comprises a device adapted to lift the support structure.

The device for reducing the distance between the surface of the liquid and a support structure solves the problem of providing portions of a rigid body on a support structure with minimal physical damage to the portions.

In certain embodiments, the device for reducing the distance between the surface of the liquid and a support structure is controlled by the control device. This advantageously allows an automated operation of the device for reducing the distance between the surface of the liquid and a support structure.

In certain embodiments, the device comprises a loop, particularly a closed loop, which is moveable at the surface of the liquid, Advantageously, portions of a rigid body may be moved at the surface of the liquid by means of the loop.

In certain embodiments, the loop exhibits a diameter of 0.005 to 1 mm, particularly 0.05 to 0.4 mm.

According to a third aspect of the invention, a system for manipulating at least one portion of a rigid body is provided, wherein the system comprises a device for manipulating at least one portion of a rigid body according to the second aspect of the invention, and ultrathin-sectionable material.

In certain embodiments, the ultrathin-sectionable material is comprised in a rigid body, wherein in the rigid body a magnetic or magnetizable material is distributed, and/or the rigid body is mechanically connected to a body of magnetic or magnetizable material.

In certain embodiments, the ultrathin-sectionable material is comprised in a rigid body or a part of a rigid body, comprising an embedding material, more particularly an epoxy resin, wherein the ultrathin-sectionable material is embedded in the embedding material.

In certain embodiments, the ultrathin-sectionable material is comprised in at least one and particularly a plurality of portions of a rigid body comprising ultrathin-sectionable material, wherein the portions have a thickness of 1 to 100000 nanometers, particularly 5 to 20000 nanometers, more particularly 5 to 500 nanometers, and a width from 50 micrometers to 3 centimeters, particularly 100 micrometers to 2 centimeters.

In certain embodiments, the ultrathin-sectionable material comprises a biological material, particularly a tissue.

In certain embodiments the rigid body is a tissue block.

In certain embodiments, a cross section of the rigid body has a shape of a polygon comprising a first edge, a second edge, a third edge, and a fourth edge, wherein the first edge and the second edge are parallel. Therein, directly connected pairs of the first edge, the second edge, the third edge, and the fourth edge form an acute angle, that is an angle of less than 90°, or an obtuse angle, that is an angle between 90° and 180°.

In certain embodiments, the cross section resembles a parallelogram and the three-dimensional shape of the rigid body resembles a parallelepiped.

The term "directly connected pairs of edges" designates two edges of the cross section, wherein no additional edge connects the two edges. In particular, the first edge and the third edge, the first edge and the fourth edge, the second edge and third edge, and the second edge and the fourth edge may be directly connected.

In certain embodiments, the third edge and the fourth edge are parallel.

In certain embodiments, a cross section of the rigid body has a shape of a polygon, wherein at least two edges of the polygon resemble an interpolation of a function having the general formula $f(x)=-a \cdot x^2$, wherein a is a positive number, and wherein the graph of the function is a parabola, and wherein the apex of the parabola is positioned at the upper boundary of the graph.

In certain embodiments, a cross section of the rigid body has a shape of a polygon comprising a first edge and a second edge, wherein the first edge and the second edge are directly connected by a third edge, and wherein the first edge and the second edge are connected by means of a plurality of edges, wherein the plurality of edges form a zig-zag line.

In certain embodiments, the first edge and the third edge form an angle of 90°.

In certain embodiments, the second edge and the third edge form an angle of 90°.

In certain embodiments, the plurality of edges forming a zig-zag line comprises an even number of edges.

In certain embodiments, the plurality of edges forming a zig-zag line comprises two edges, four edges, six edges, or eight edges.

In certain embodiments, the cross section of the rigid body comprises a fourth edge comprised in the plurality of edges forming a zig-zag line, wherein the fourth edge is directly connected to the first edge, and wherein the fourth edge and the first edge form an angle of less than 90°.

In certain embodiments, the cross section of the rigid body comprises a fourth edge comprised in the plurality of edges forming a zig-zag line, wherein the fourth edge is directly connected to the first edge, and wherein the fourth edge and the first edge form an angle between 90° and 180°.

In certain embodiments, the cross section of the rigid body comprises a fifth edge comprised in the plurality of edges forming a zig-zag line, wherein the fifth edge is directly connected to the second edge, and wherein the fifth edge and the second edge form an angle of less than 90°.

In certain embodiments, the cross section of the rigid body comprises a fifth edge comprised in the plurality of edges forming a zig-zag line, wherein the fifth edge is directly connected to the second edge, and wherein the fifth edge and the second edge form an angle between 90° and 180°.

In contrast to a cuboid shape of a rigid body, particularly a tissue block, known in the prior art, the shapes of the rigid body described herein generate forces during cutting, which lead to a detachment of two adjacent sections, which are cut from the rigid body using a cutting device, particularly a diamond knife, more particularly adapted for ultramicrotomy, most particularly an oscillating diamond knife.

Advantageously, an oscillating diamond knife allows an easier detachment of adjacent sections.

This advantageously allows better individual handling of portions of a rigid body, particularly sections of a rigid body, at the surface of the liquid contained in the reservoir. In certain embodiments, the cross section of the rigid body comprises a fifth edge, which is non-parallel to the first edge, and the second edge, and the third edge, and the fourth edge. In certain embodiments, the cross section resembles a pentagon with two pairs of parallel edges, which can also be described as a parallelogram with one corner cut off. In particular, the three-dimensional shape of the rigid body resembles a pentagonal prism.

Advantageously, a rigid body with a pentagonal cross section has been observed to be mechanically more stable compared to a rigid body with a parallelogram-shaped cross section.

In certain embodiments, the rigid body has a three-dimensional shape of a cylinder, a sphere, an ellipsoid or a prism, particularly a cuboid.

In certain embodiments, a cross section of the rigid body, particularly the tissue block, resembles the shape of a portion of a rigid body, particularly a portion of a rigid body comprising biological material, wherein the portion has been provided by cutting the portion from the rigid body.

In certain embodiments, the rigid body comprises a first layer comprising a magnetic or magnetizable material and/or a second layer comprising the ultrathin-sectionable material, wherein particularly the first layer and/or the second layer comprises an embedding material, particularly an epoxy resin.

In certain embodiments, the rigid body comprises a first layer comprising a magnetic or magnetizable material, a second layer comprising the ultrathin-sectionable material, and a third layer comprising a connecting material, particularly an epoxy resin, particularly wherein the third layer is mechanically connected to the first layer and wherein the third layer is mechanically connected to the second layer.

In certain embodiments, the rigid body comprises a fourth layer comprising a connecting material, particularly comprising an epoxy resin, particularly wherein the fourth layer is mechanically connected to the first layer.

In certain embodiments, the rigid body comprises a fourth layer comprising a connecting material, particularly comprising an epoxy resin, and a fifth layer comprising ultrathin-sectionable material, more particularly wherein the fourth layer is mechanically connected to the first layer, and wherein particularly the fifth layer is mechanically connected to the fourth layer.

In certain embodiments, the ultrathin-sectionable material comprises a biological material.

In certain embodiments, the ultrathin-sectionable material comprises a biological material comprising an isolated component of an animal body, more particularly a human body or an isolated component of a plant body, particularly an animal tissue or a plant tissue or a human tissue, more particularly a brain tissue.

In certain embodiments, the ultrathin-sectionable material comprises a biological material comprising a plurality of microorganisms, particularly bacteria, archaea, or fungi, more particularly a biofilm comprising bacteria, archaea, or fungi.

In certain embodiments, the ultrathin-sectionable material comprises a biological material comprising a plurality of cells, particularly bacterial cells, or archaeal cells, or eukaryotic cells, particularly human cells, or animal cells, or plant cells.

In certain embodiments, the ultrathin-sectionable material comprises a biological material comprising an extracellular matrix, particularly comprising a collagen, or a proteoglycan, or a glycoprotein.

In certain embodiments, the ultrathin-sectionable material comprises a biological material comprising at least one protein and/or at least one polysaccharide, and/or at least one lipid, and/or at least one nucleic acid, particularly at least one deoxyribonucleic acid (DNA) molecule and/or at least one ribonucleic acid (RNA) molecule.

In certain embodiments, the rigid body comprises at least one marker particle, wherein the marker particle can be visualized by an imaging technique, particularly photography, electron microscopy, or light microscopy, more particularly fluorescence microscopy.

In certain embodiments, the minimal extension of the marker particle is between 2 nanometers and 5 micrometers, particularly between 5 nanometers and 1 micrometer.

In certain embodiments, the marker particle is fluorescent or comprises a fluorescent substance.

In certain embodiments, the portion of a rigid body comprises at least one segment of a marker particle, particularly a segment generated by cutting of the marker particle.

According to a fourth aspect of the invention, a computer program comprising a program code for the execution of the steps of the method described herein, when the computer program is loaded or executed on a computer, is provided.

In certain embodiments, the computer program is adapted to access and/or control the controlling device, particularly in order to execute steps of the method described herein, in particular moving a moving device in order to move a permanent magnet, activating an actuator, activating an electromagnet, such that the electromagnet produces a magnetic field, moving a floatable device, particularly a floatable magnetic barrier or a floatable knife, and/or controlling a device for reducing the distance between the surface of the liquid and a support structure, particularly a syringe pump.

In certain embodiments, the computer program is adapted to execute the steps for taking images, particularly high resolution images, more particularly light microscopic or electron microscopic images, and/or generating a data set for each portion of a rigid body of the at least one image, and/or comparing at least one value of the data sets, and/or determining those data sets having a minimal difference of the respective value with respect to each other, and/or generating an order of the data sets by evaluating the respective minimal differences.

In certain embodiments, the computer program is adapted to execute the steps for taking at least one image, particularly a high resolution image, of a plurality of portions of a rigid body.

In certain embodiments, the computer program is adapted to execute the steps for generating a data set for each portion of a rigid body displayed on the at least one image.

In certain embodiments, the computer program is adapted to execute the steps for comparing pairs of data sets, particularly each pair of data sets.

In certain embodiments, the computer program is adapted to execute the steps for determining a distance value for pairs of data sets, particularly each pair of data sets, wherein the distance value reflects the similarity or dissimilarity of the respective pair of data sets.

In certain embodiments, the computer program is adapted to execute the steps for generating an order or a plurality of orders of the data sets.

In certain embodiments, the computer program is adapted to execute the steps for determining the sum of distance values of neighboring pairs of data sets of the respective order.

In certain embodiments, the computer program is adapted to execute the steps for comparing the sums of distance values of the generated orders.

In certain embodiments, the computer program is adapted to execute the steps for calculating the sum of distance values reflecting the similarity or dissimilarity.

In certain embodiments, the computer program is adapted to execute the steps for selecting the order having the maximal sum of distance values reflecting the similarity, or having the minimal sum of distance values reflecting the dissimilarity.

In certain embodiments, the order, in which portions of a rigid body have been cut from a rigid body, is determined using the computer program.

Advantageously, a computer program may provide inputs to the control device, thus allowing an automated operation of the device for manipulating at least one portion of a rigid body.

Advantageously, the computer program may be used to determine the order, in which portions of a rigid body have been cut from a rigid body. This allows the reconstruction of three-dimensional structures of the investigated ultrathin-sectionable material by combination of two-dimensional images of sections of ultrathin-sectionable material.

The following further aspects and embodiments of the rigid body are stated as items, which may also be formulated as claims.

Item 1: A rigid body comprising an ultrathin-sectionable, particularly a biological, material and a magnetic or magnetizable material, characterized in that the magnetic or magnetizable material is distributed in the rigid body and/or the rigid body is mechanically connected to a body comprising magnetic or magnetizable material.

Item 2: The rigid body according to item 1, wherein a cross section of the rigid body has a shape of a polygon comprising a first edge, a second edge, a third edge, and a fourth edge, and wherein the first edge and the second edge are parallel, and wherein directly connected pairs of the first edge, the second edge, the third edge, and the fourth edge form an acute angle or an obtuse angle.

Item 3: The rigid body according to item 2, wherein the third edge and the fourth edge are parallel.

Item 4: The rigid body according to item 2 or 3 wherein the cross section of the rigid body comprises a fifth edge, which is non-parallel to the first, second, third, and fourth edge.

Item 5: The rigid body according to item 1, wherein a cross section of the rigid body has a shape of a polygon, and wherein at least two edges of the polygon resemble an interpolation of a function having the general formula $f(x)= -a \cdot x^2$.

Item 6: The rigid body according to item 1, wherein a cross section of the rigid body has a shape of a polygon comprising a first edge, and a second edge, which are directly connected by a third edge, wherein the first edge and the second edge are connected by means of a plurality of edges, wherein said plurality of edges form a zig-zag line.

Item 7: The rigid body according to any one of the preceding items, wherein the rigid body comprises an embedding material, particularly an epoxy resin.

Item 8: The rigid body according to item 7, wherein the ultrathin-sectionable material is embedded in the embedding material.

Item 9: The rigid body according to any one of the preceding items, wherein the rigid body comprises a first layer comprising the magnetic or magnetizable material, and a second layer comprising the ultrathin-sectionable material.

Item 10: The rigid body according to item 9, wherein the rigid body comprises a first layer comprising a magnetic or magnetizable material, a second layer comprising the ultrathin-sectionable material, and a third layer comprising a connecting material, particularly an epoxy resin, particularly wherein the third layer is mechanically connected to the first layer and wherein the third layer is mechanically connected to the second layer.

Item 11: The rigid body according to item 9 or 10, wherein the rigid body comprises a fourth layer comprising a connecting material, particularly comprising an epoxy resin, particularly wherein the fourth layer is mechanically connected to the first layer.

Item 12: The rigid body according to any one of the items 9 to 11, wherein the rigid body comprises a fourth layer comprising a connecting material, particularly comprising an epoxy resin, and a fifth layer comprising ultrathin-sectionable material, wherein particularly the fourth layer is mechanically connected to the first layer, and wherein particularly the fifth layer is mechanically connected to the fourth layer.

Item 13: The rigid body according to any one of the items 10 to 12, wherein the third layer is mechanically connected to the ultrathin-sectionable material of the second layer.

Item 14: The rigid body according to any one of the items 10 to 12, wherein the third layer is mechanically connected to the embedding material of the second layer.

Item 15: The rigid body according to any one of the preceding items, wherein the ultrathin-sectionable material comprises a biological material, particularly comprising a tissue, more particularly an animal or a human tissue, most particularly a brain tissue.

Item 16: The rigid body according to any one of the preceding items, wherein the rigid body comprises at least one marker particle, wherein the marker particle can be visualized by an imaging technique, particularly photography, electron microscopy, or light microscopy, more particularly fluorescence microscopy.

Item 17: The rigid body according to item 16, wherein the minimal extension of the marker particle is between 2 nanometers and 5 micrometers, particularly between 5 nanometers and 1 micrometer.

Item 18: The rigid body according to any one of the items 16 and 17, wherein the marker particle is fluorescent or comprises a fluorescent substance.

Wherever alternatives for single separable features are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

SHORT DESCRIPTION OF THE FIGURES

DETAILED DESCRIPTION OF THE FIGURES

Figure 1:
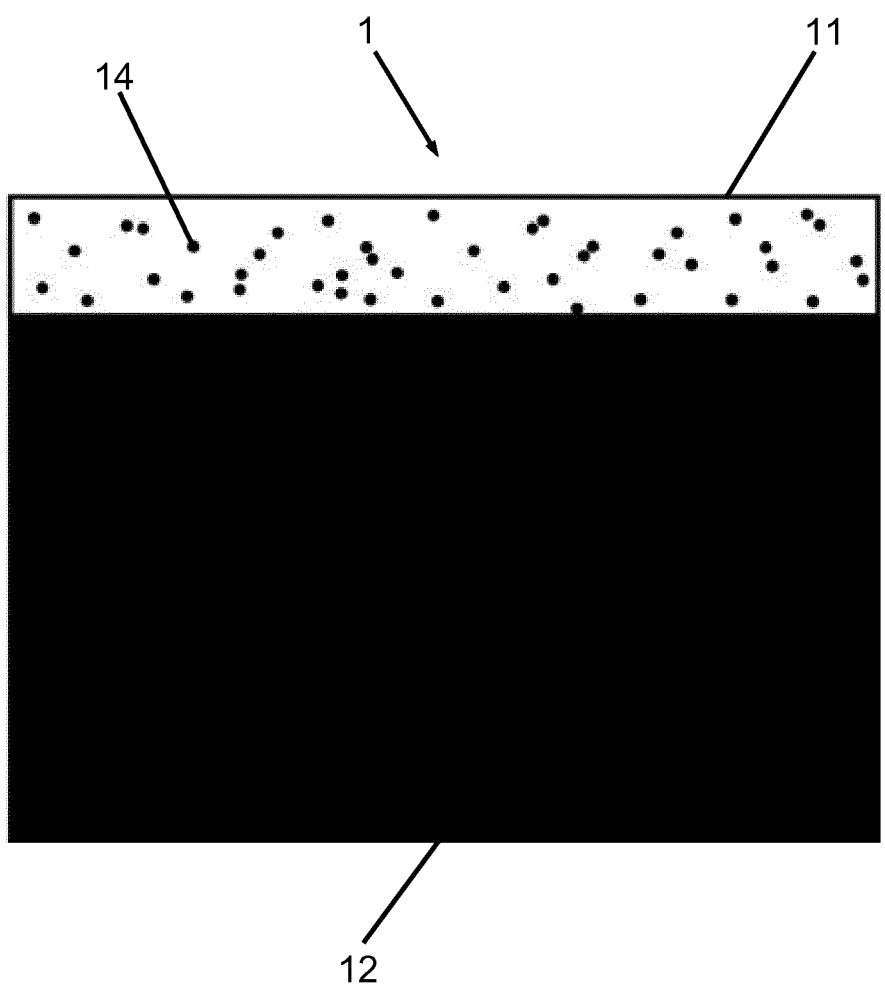
FIG. 1 shows a cross section of a rigid body comprising a first layer comprising a magnetic or magnetizable material and a second layer comprising an ultrathin-sectionable material.

Specifically, FIG. 1 shows a rectangular cross section of a rigid body 1, wherein the rigid body 1 comprises a first layer 11 comprising a magnetic or magnetizable material 14, particularly superparamagnetic nanoparticles, and a first embedding material, particularly an epoxy resin, wherein the magnetic or magnetizable material 14 is distributed in the first embedding material. The rigid body 1 further comprises a second layer 12 comprising an ultrathin-sectionable, particularly biological, material and comprising a second embedding material, particularly an epoxy resin, and wherein the ultrathin-sectionable, particularly biological, material is embedded in the second embedding material. The second layer 12 is mechanically connected to the first layer 11, particularly mechanically connected to the first embedding material. The first layer 11 particularly covers at least one of the six faces of the rigid body 1. The magnetic or magnetizable material 14 is distributed in the first layer 11, so that a portion 20 of a rigid body 1 with a thickness between 1 and 100000 nm, particularly between 1 and 1000 nm, which has been cut from the rigid body 1, contains a sufficient amount of magnetic or magnetizable material 14, so that a magnetic field provided by a magnetic device positioned near the surface of the liquid contained in a reservoir will result in a magnetic force acting on the portion 20, while the portion 20 is floating on the surface of the liquid contained in the reservoir.

For example, the rigid body 1 may be produced by applying a viscous epoxy resin comprising magnetic or magnetizable material 14 onto a second layer 12 comprising an embedding material and an ultrathin-sectionable, particularly biological, material, polymerization of the epoxy resin and, optionally, trimming of the rigid body 1 to result in a desired shape.

Figure 2:
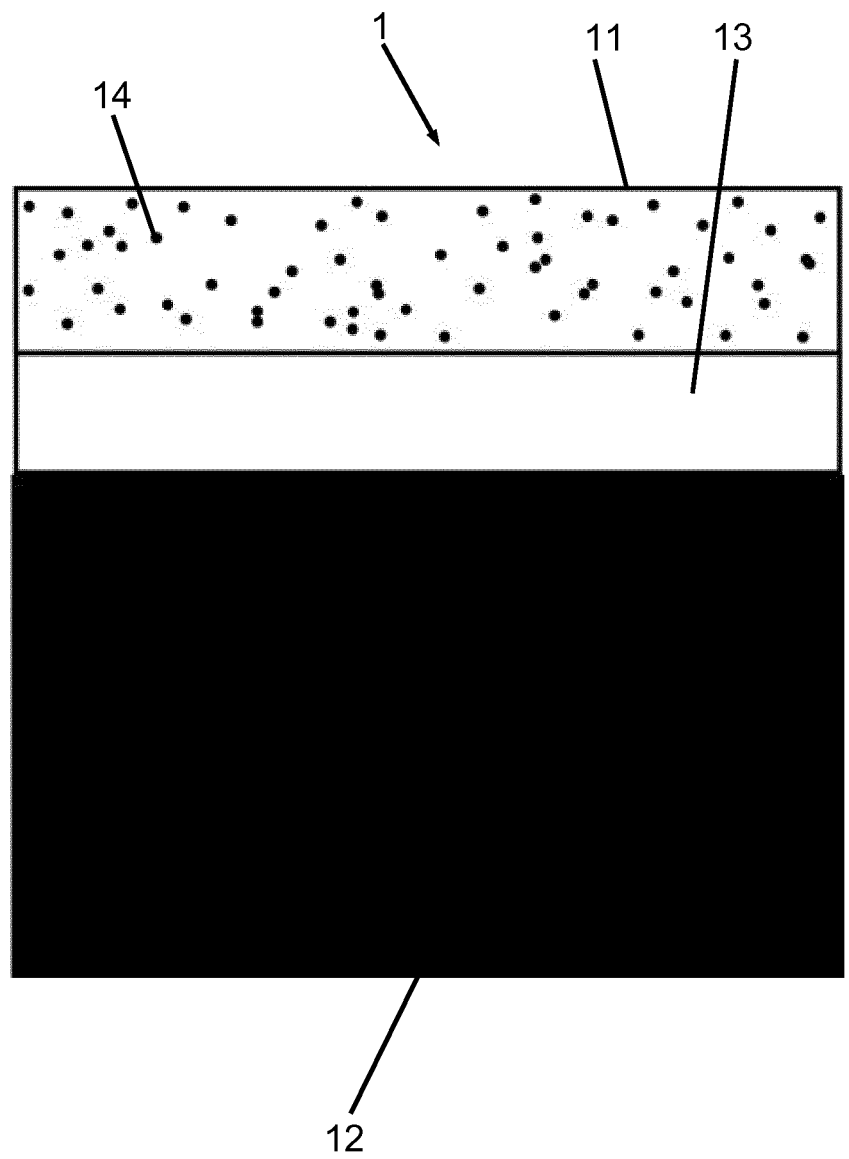
FIG. 2 shows a cross section of a rigid body comprising a first layer comprising a magnetic or magnetizable material, a second layer comprising an ultrathin-sectionable material, and a third layer comprising a connecting material.

FIG. 2 shows a rectangular cross section of a rigid body 1, wherein the rigid body 1 comprises a first layer 11 comprising a magnetic or magnetizable material 14, particularly superparamagnetic nanoparticles, and a first embedding material, such as an epoxy resin, wherein the magnetic or magnetizable material 14 is distributed in the first embedding material, a second layer 12 comprising an ultrathin-sectionable, particularly biological, material, and comprising a second embedding material, particularly an epoxy resin, and wherein the ultrathin-sectionable, particularly biological, material is embedded in the second embedding material. The rigid body 1 further comprises a third layer 13 comprising a connecting material, particularly an epoxy resin. The first layer 11 comprising magnetic or magnetizable material 14 is mechanically connected to the third layer 13, and the third layer 13 is mechanically connected to the second layer 12 comprising an ultrathin-sectionable, particularly biological, material, particularly mechanically connected to the second embedding material. The first layer 11 comprising magnetic or magnetizable material 14 and the third layer 13 particularly cover at least one of the six faces of the rigid body 1, wherein the third layer 13 particularly covers at least one of the six faces of the rigid body 1 and the first layer 11 comprising magnetic or magnetizable material 14 particularly covers the complete third layer 13. The magnetic or magnetizable material 14 is distributed in the first layer 11, so that a portion 20 of a rigid body 1 of approximately 1 to 100000 nm, particularly 1 to 1000 nm, thickness, which has been cut from the rigid body 1, contains a sufficient amount of magnetic or magnetizable material 14, so that a magnetic field provided by a magnetic device positioned near the surface of the liquid contained in a reservoir will result in a magnetic force acting on the portion 20, while the portion 20 is floating at the surface of the liquid contained in the reservoir.

For example, the rigid body 1 may be provided by applying a viscous connecting material, particularly an epoxy resin, onto a first block comprising a first embedding material, in which magnetic or magnetizable material 14 is distributed, providing a second block comprising polymerized epoxy resin and an ultrathin-sectionable, particularly biological, material, attaching the second block to the connecting material, polymerizing the connecting material, and, optionally, trimming of the rigid body 1 to result in a desired shape of the rigid body 1.

Figure 3:
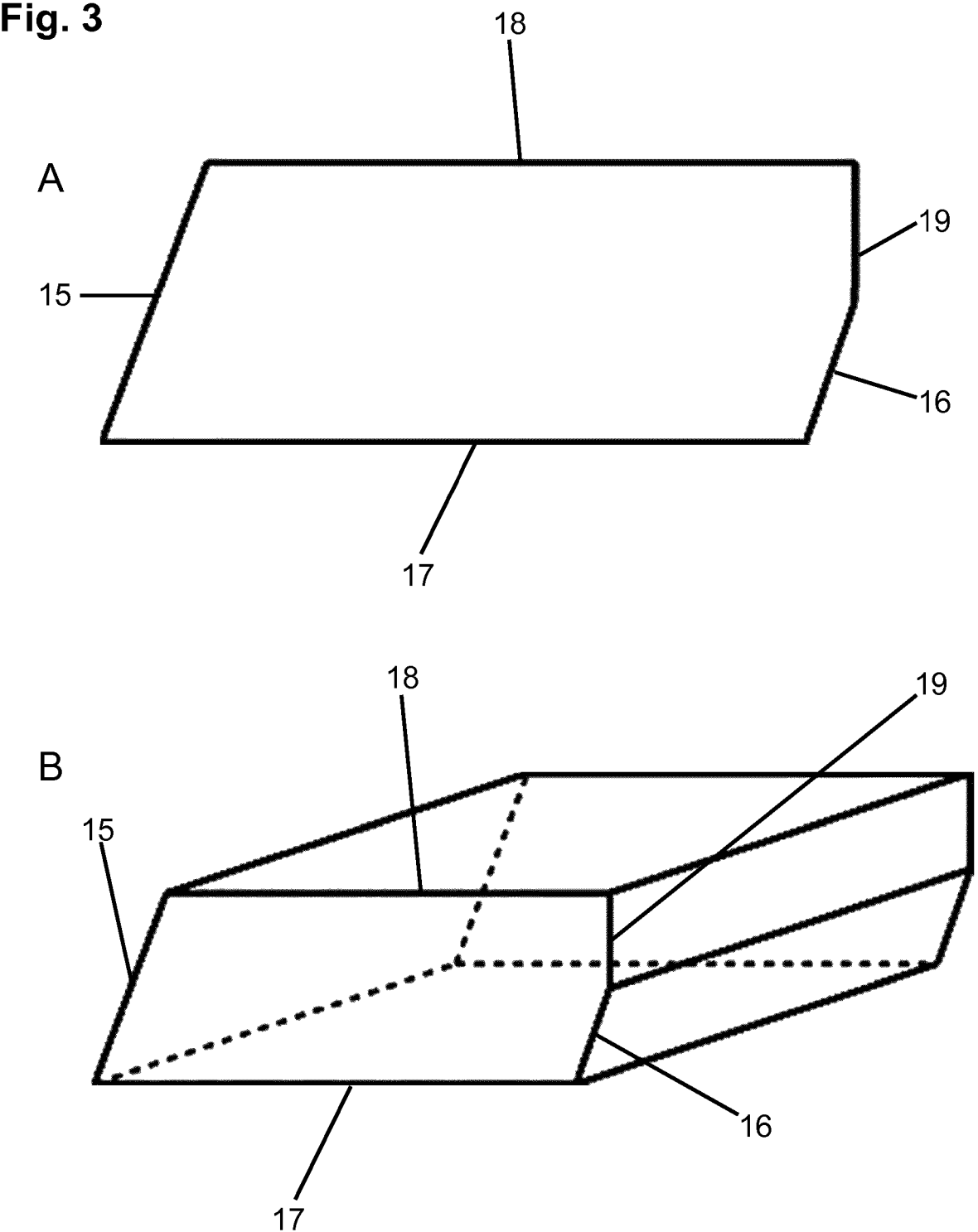
FIG. 3 shows a rigid body.

FIG. 3 shows a cross section of a rigid body 1 (FIG. 3A), and a perspective view of a rigid body 1 (FIG. 3B). The cross section (FIG. 3A) has the shape of a pentagon with a first edge 15 and a second edge 16, wherein the first edge 15 and the second edge 16 are parallel, and a third edge 17 and a fourth edge 18, wherein the third edge 17 and the fourth edge 18 are parallel. This shape can also be described as a parallelogram with one corner cut off. The fifth edge 19 of the cross section is not parallel to the first edge 15 and the second edge 16 and the fifth edge 19 is not parallel to the third edge 17 and the fourth edge 18.

As shown in the perspective view (FIG. 3B), the rigid body 1 has the three-dimensional shape of a prism with a base having the shape of the cross section depicted in FIG. 3A. The three-dimensional shape of the rigid body 1 can also be described as a parallelepiped with a section cut off.

The depicted cross section (FIG. 3A) resembles a shape of a portion 20 of a rigid body 1, which has been cut from a rigid body 1 having a shape displayed as a perspective view in (FIG. 3B).

This shape of portions 20 of a rigid body 1 is advantageous for manipulating individual portions 20 at the surface of the liquid contained in a reservoir, because adhesion of consecutive portions 20 to each other is reduced due to the shape. As a result, the tendency of chain formation of portions 20 during a cutting session is reduced and portions 20 adhering to each other are easier to separate due the block shape provided by the invention. Including a fifth edge 19 into the cross section of the block is advantageous because it could be observed that this additional edge stabilizes the rigid body 1 and the resulting portions 20.

Figure 4:
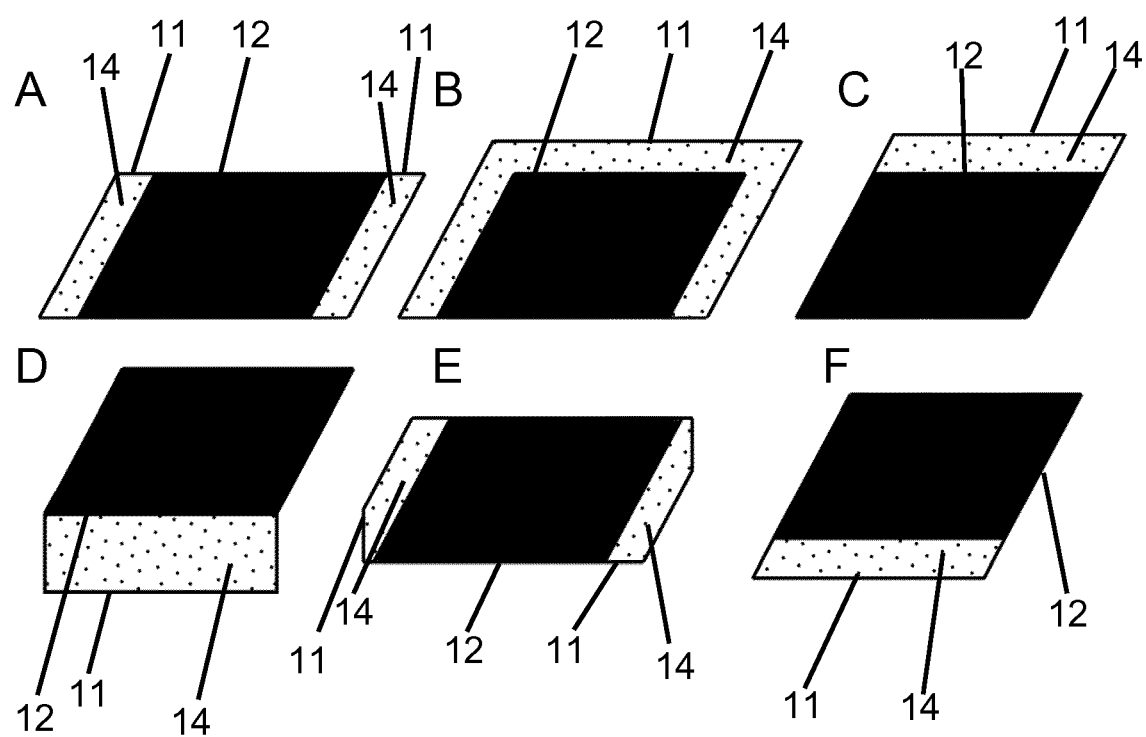
FIG. 4 shows cross sections of rigid bodies comprising a magnetic or magnetizable material.

Specifically, FIG. 4 shows cross sections of rigid bodies 1 comprising at least one first layer 11 comprising a magnetic or magnetizable material.

In FIG. 4A, a cross section of a rigid body 1 having a shape of a parallelogram and comprising two first layers 11 comprising a magnetic or magnetizable material 14 is depicted, wherein the two first layers 11 comprising a magnetic or magnetizable material 14 cover opposite faces of the parallelepiped shaped rigid body 1.

In FIG. 4B, a cross section of a rigid body 1 having a shape of a parallelogram and comprising three first layers 11 comprising a magnetic or magnetizable material 14 is depicted, wherein two of the three first layers 11 comprising a magnetic or magnetizable material 14 cover opposite faces of the parallelepiped shaped rigid body 1.

In FIG. 4C, FIG. 4D, and FIG. 4F, cross sections of rigid bodies having a shape of a parallelogram and comprising a first layer 11 comprising a magnetic or magnetizable material 14 are depicted. The shape of the corresponding rigid bodies resembles parallelepipeds.

In FIG. 4E, a cross section of a rigid body 1 having the shape of a hexagon with at least a first pair of parallel edges and a second pair of parallel edges is depicted, wherein the second layer 12 comprising an ultrathin-sectionable, particularly biological, material has the shape of a parallelogram, and wherein the rigid body 1 comprises two first layers 11 comprising a magnetic or magnetizable material 14, and wherein the two first layers 11 comprising a magnetic or magnetizable material 14 cover opposite faces of the parallelepiped shaped second layer 12.

Figure 5:
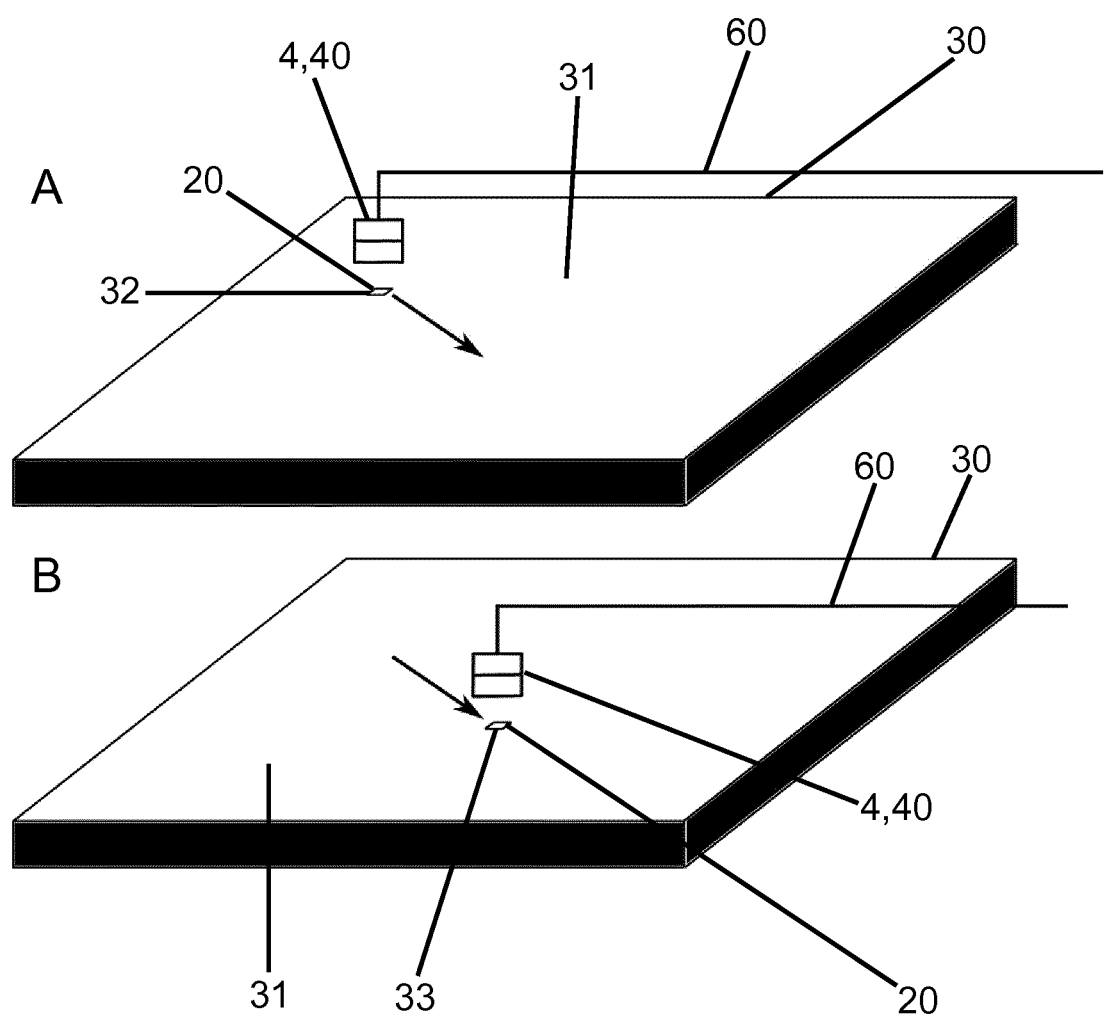
FIG. 5 shows a reservoir, a permanent magnet, which is mechanically connected to a manipulator arm, and a portion of a rigid body.

FIG. 5 shows a reservoir 30 containing a liquid, and a permanent magnet 40, which is mechanically connected to a movable manipulator arm 60, wherein the permanent magnet 40 is positioned near the surface 31 of the liquid contained in a reservoir 30, and a portion 20 a rigid body 1 comprising magnetic or magnetizable material 14 floating at the surface of the liquid.

In FIG. 5A, the portion 20 of a rigid body 1 floats at a first position 32 at the surface of the liquid 31, and the permanent magnet 40 is positioned by the manipulator arm 60 above the first position 32, such that the magnetic field provided by the permanent magnet 40 acts on the portion 20.

In FIG. 5B, the portion 20 of a rigid body 1 floats at a second position 33 at the surface 31 of the liquid contained in the reservoir 30, and the permanent magnet 40 is positioned by the manipulator arm 60 above the second position 33. The portion 20 has been moved from the first position 32 (FIG. 5A) to the second position 33 (FIG. 5B) at the surface 31 of the liquid contained in the reservoir 30 by the magnetic force provided by the magnetic field provided by the permanent magnet 40, which has been moved from a position above the first position 32 to a position above the second position 33 by a movement of the manipulator arm 60.

Figure 6:
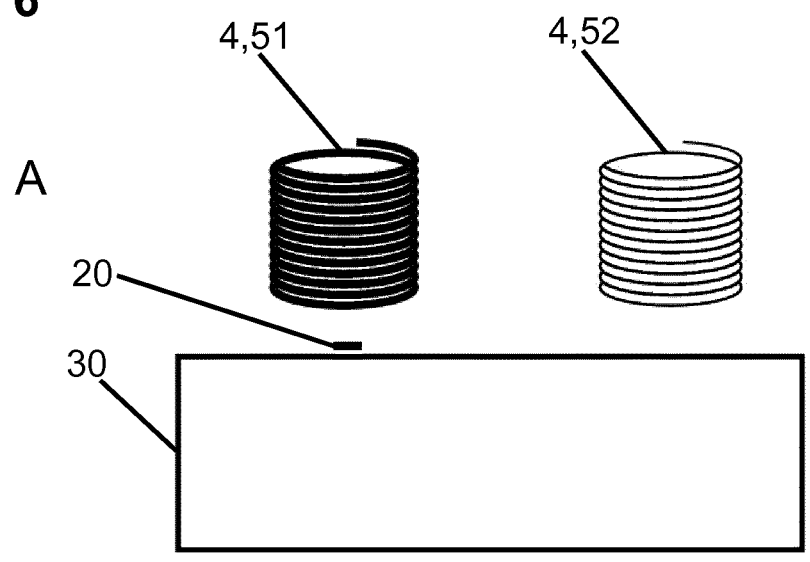
FIG. 6 shows the cross section of a reservoir, a first electromagnet, a second electromagnet, and a portion of a rigid body.
Figure 6:
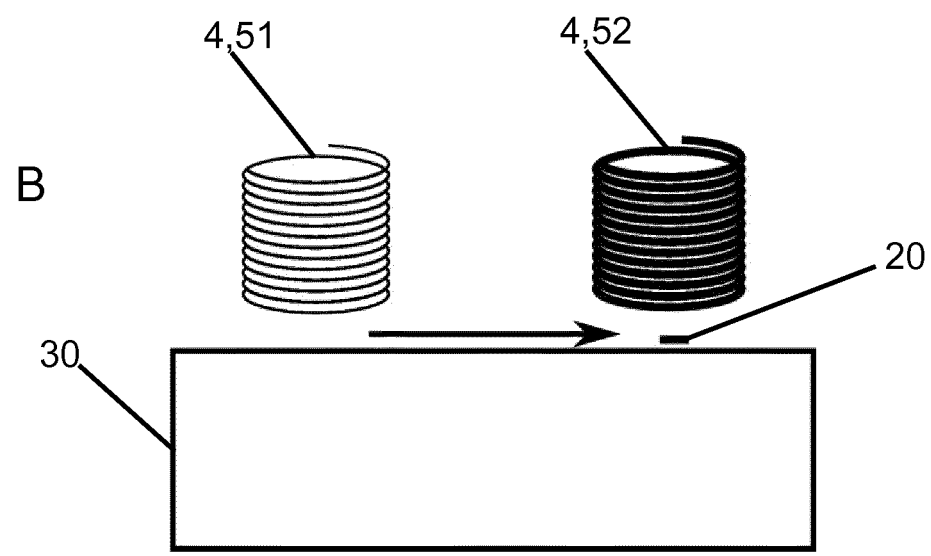

FIG. 6 shows a cross section of a reservoir 30, and a portion 20 of a rigid body 1 comprising magnetic or magnetizable material, wherein the portion 20 is floating at the surface of the liquid contained in the reservoir 30, a first electromagnet 51, wherein the first electromagnet 51 is positioned above a first position at the surface of the liquid, and a second electromagnet 52, wherein the second electromagnet 52 is positioned above a second position at the surface of the liquid.

In FIG. 6A, an electric current flows through the first electromagnet 51, which results in a magnetic field provided by the first electromagnet 51. The portion 20 of a rigid body 1 floats at the first position, and the magnetic field provides a magnetic force acting on the portion 20 floating at the surface of the liquid contained in the reservoir 30 in the vicinity of the first position.

In FIG. 6B, an electric current flows through the second electromagnet 52, which results in a magnetic field provided by the second electromagnet 52. The magnetic field provides a magnetic force acting on the portion 20 of a rigid body 1, if the portion 20 is floating at the surface of the liquid in the vicinity of the second position.

When the electric current through the first electromagnet 51 is switched off and the electric current through the second electromagnet 52 is switched on in a situation, in which the portion 20 of a rigid body 1 floats at the surface in the vicinity of the first position, the magnetic force acting on the portion 20 results in a movement of the portion 20 from the vicinity of the first position to the second position at the surface of the liquid (FIG. 6C).

Figure 7:
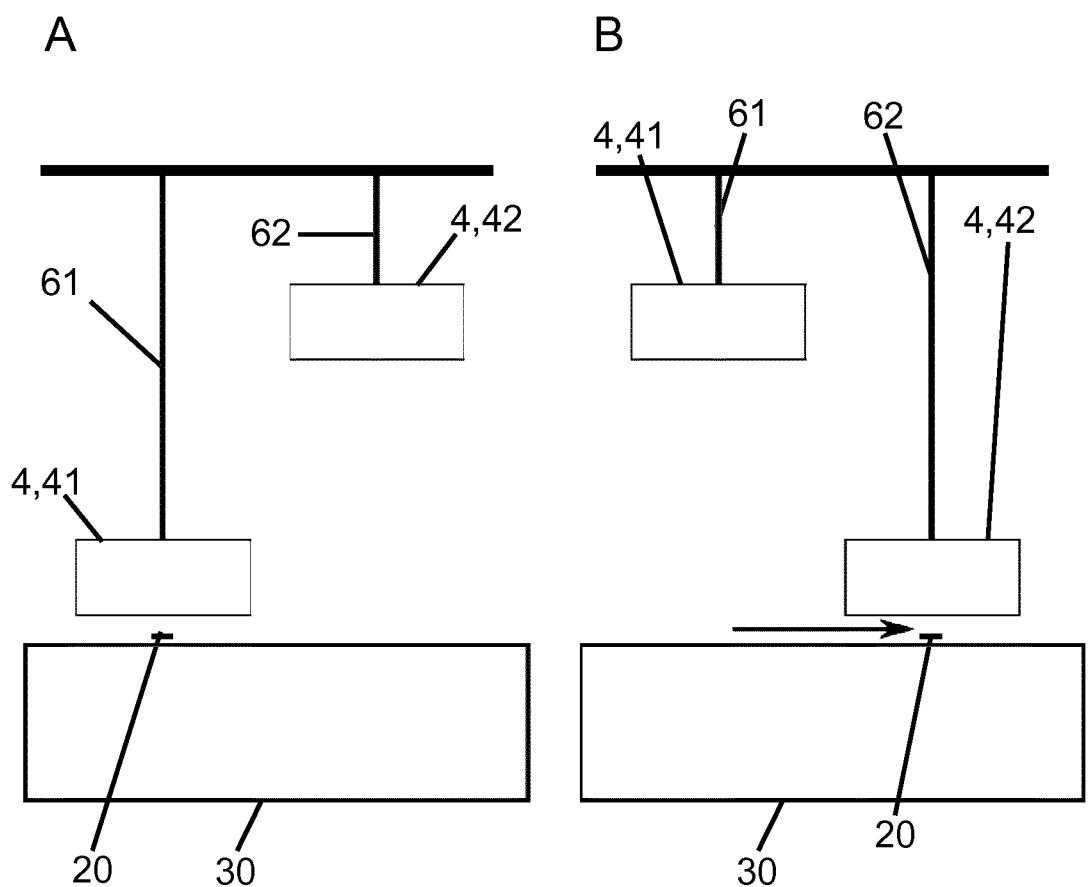
FIG. 7 shows a cross section of a reservoir, a first permanent magnet, a second permanent magnet, a first actuator, a second actuator, and a portion of a rigid body.

FIG. 7 shows a cross section of a reservoir 30 containing a liquid, a portion 20 of a rigid body 1 floating at the surface of the liquid contained in the reservoir 30, and a first permanent magnet 41, wherein the first permanent magnet 41 is mechanically connected to a first actuator 61, and wherein the first permanent magnet 41 is positioned above a first position at the surface of the liquid, a second permanent magnet 42, wherein the second permanent magnet 42 is mechanically connected to the second actuator 62, and wherein the second permanent magnet 42 is positioned above a second position at the surface of the liquid. The first actuator 61 is adapted to change the distance between the first permanent magnet 41 and the surface of the liquid, and the second actuator 62 is adapted to change the distance between the second permanent magnet 42 and the surface of the liquid.

In FIG. 7A, the portion 20 of a rigid body 1 is positioned at the first position, and the first permanent magnet 41 is positioned above the first position, wherein the first permanent magnet 41 exhibits a first distance to the first position at the surface of the liquid, so that the magnetic field provided by the first permanent magnet 41 provides a magnetic force acting on the portion 20 floating at the surface of the liquid in the vicinity of the first position. The second permanent magnet 42 is positioned at a position above the second position, wherein the second permanent magnet 42 exhibits a second distance to the second position at the surface of the liquid, and wherein the second distance is greater than the first distance, so that the magnetic field at the surface of the liquid provided by the second permanent magnet 42 is too weak to provide a sufficient magnetic force to move the portion 20 at the surface of the liquid.

In FIG. 7B, the first permanent magnet 41 is positioned at a position above the first position, wherein the first permanent magnet 41 exhibits a first distance to the first position at the surface of the liquid, so that the magnetic field at the surface of the liquid provided by the first permanent magnet 41 is too weak to provide a sufficient magnetic force to move the portion 20 of a rigid body 1 floating at the surface of the liquid. The second permanent magnet 42 is positioned at a position above the second position, wherein the second permanent magnet 42 exhibits a second distance to the second position at the surface of the liquid, and wherein the second distance is smaller than the first distance, so that the magnetic field provided by the second permanent magnet 42 provides a magnetic force acting on the portion 20 floating at the surface of the liquid in the vicinity of the second position.

When the first permanent magnet 41 is moved away from the surface of the liquid by the first actuator 61, and the second permanent magnet 42 is moved closer to the surface of the liquid by the second actuator 62 in a situation, in which the portion 20 of a rigid body 1 floats at the surface in the vicinity of the first position, the magnetic force acting on the portion 20 results in a movement of the portion 20 from the vicinity of the first position to the second position at the surface of the liquid.

Figure 8:
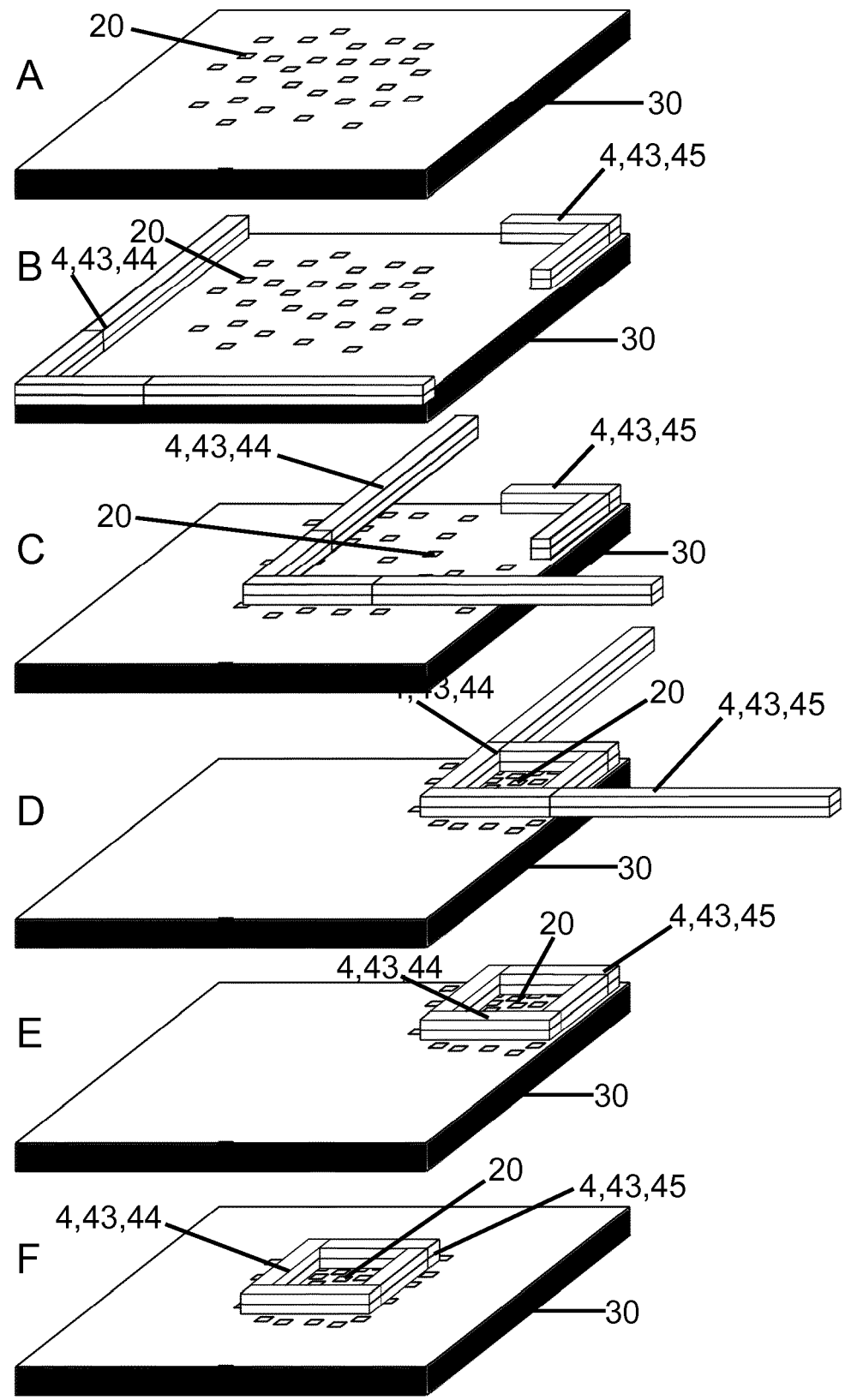
FIG. 8 shows a reservoir, a first magnetic barrier, a second magnetic barrier, and a plurality of portions of a rigid body.

Specifically, FIG. 8A shows a perspective view of a reservoir 30 and a plurality of portions 20 of a rigid body 1, wherein each portion 20 of a rigid body 1 is floating at the surface of the liquid contained in the reservoir 30. In addition, FIG. 8B shows a first magnetic barrier 44 comprising at least one permanent magnet, wherein the first magnetic barrier 44 floats at a first position at the surface of the liquid contained in the reservoir 30, and a second magnetic barrier 45 comprising at least one permanent magnet, wherein the second magnetic barrier 45 floats at a second position at the surface of the liquid contained in the reservoir 30.

FIG. 8C shows the first magnetic barrier 44 at a third position at the surface of the liquid, wherein the plurality of portions 20 of a rigid body 1 has been moved by a magnetic force acting on the portions 20 as a result of a magnetic field provided by the first magnetic barrier 44 to the vicinity of a first area, wherein the first area is restricted on two sides by the first magnetic barrier 44.

FIG. 8D shows the first magnetic barrier 44 at a third position at the surface of the liquid, wherein the third position is in the vicinity of the second position, and wherein the plurality of portions 20 of a rigid body 1 has been moved to the vicinity of a second area having the shape of a rectangle, wherein the second area is restricted on two adjacent sides by a first part of the first magnetic barrier 44 and on the two remaining adjacent sides by the second magnetic barrier 45, and wherein a second part of the first magnetic barrier 44 has been removed from the first magnetic barrier 44.

FIG. 8E shows a third area restricted by the first magnetic barrier 44 and the second magnetic barrier 45, wherein the third area is positioned in the vicinity of the center of the surface of the liquid contained in the reservoir 30. The plurality of portions 20 of a rigid body 1 has been moved to the vicinity of the center of the surface of the liquid by a magnetic force acting on the portions 20 of a rigid body 1 as a result of a magnetic field provided by the first magnetic barrier 44 and the second magnetic barrier 45. Therefore, an area of the liquid surface as well as a plurality of portions 20 is enclosed by the magnetic barriers.

In a temporal order FIG. 8A to FIG. 8E depict a sequence of events, in which the first magnetic barrier 44 and the second magnetic barrier 45 are positioned in the reservoir 30 (FIG. 8B), the first magnetic barrier 44 is moved in order to accumulate the plurality of portions 20 of a rigid body 1 in the vicinity of the first area (FIG. 8C). The first magnetic barrier 44 is then moved further, so that the plurality of portions 20 is accumulated in the vicinity of the second area by the magnetic force acting on the portions 20 (FIG. 8D). A first part of the first magnetic barrier 44 is then removed (FIG. 8E). Finally, the first magnetic barrier 44 and the second magnetic barrier 45 are moved to the third area (FIG. 8F). Thereby the plurality of portions 20 is moved to the vicinity of the third area by the magnetic force.

In this way, the density of portions 20 can be increased and portions 20 can be moved to specific positions at the surface of the liquid contained in the reservoir 30, for instance above a support structure, such as an imaging grid or a silicon wafer. Subsequently, the distance of the support structure to the surface of the liquid can be reduced, for example by removing liquid from the reservoir 30, so that the portions 20 are carried by the support structure. The support structure can then be removed, dried, and the portions 20 can be subjected to microscopic imaging.

Figure 9:
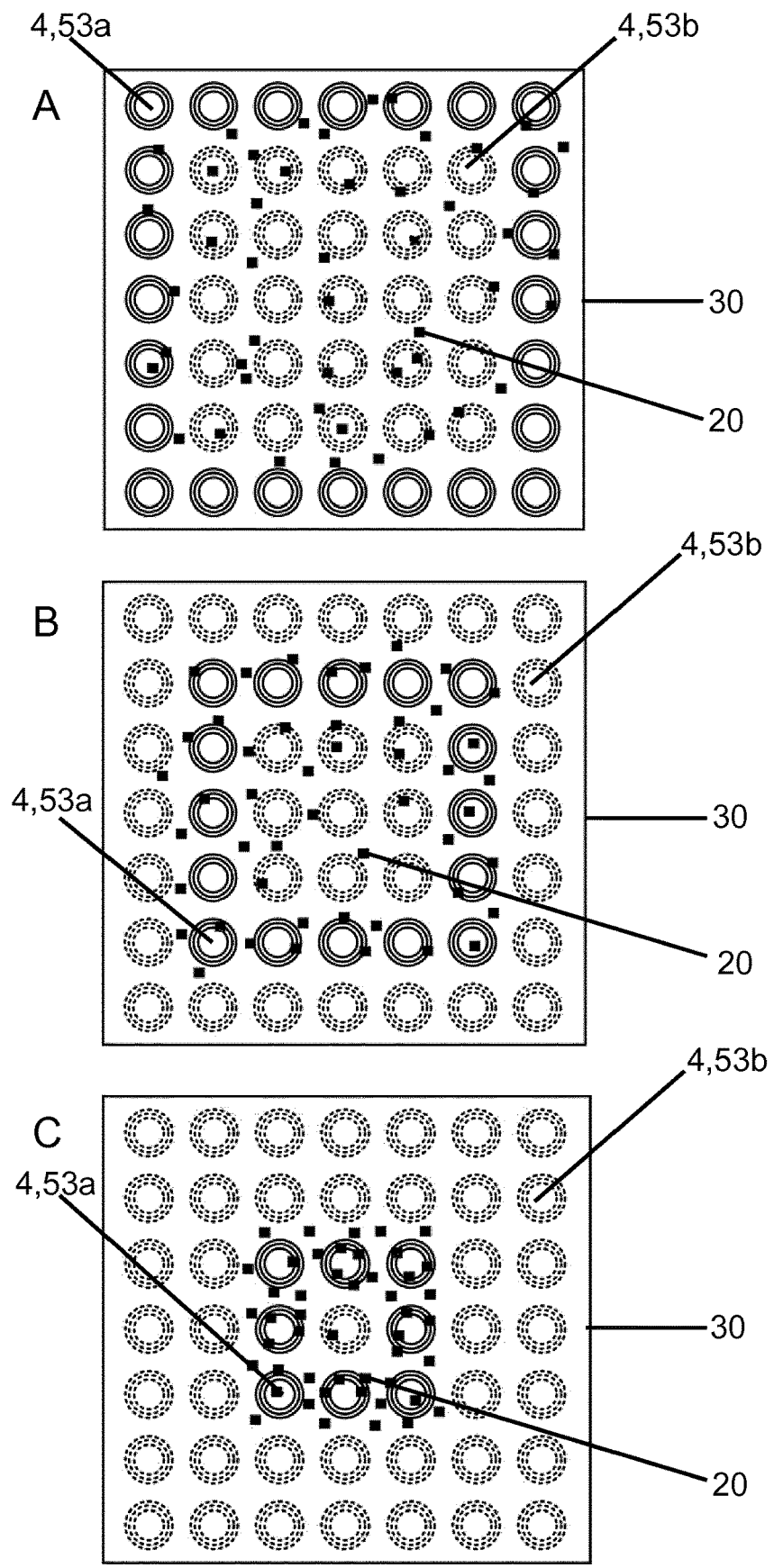
FIG. 9 shows a top view of a reservoir, an array of electromagnets, and a plurality of portions of a rigid body.

Specifically, FIG. 9 shows a top view of a reservoir 30 and an array comprising a plurality of electromagnets 53a, 53b, wherein the array is positioned above the surface of the liquid contained in the reservoir 30, and a plurality of portions 20 of a rigid body 1 comprising a magnetic or magnetizable material. The distance of the array to the surface of the liquid contained in the reservoir 30 is such that a magnetic field provided by an electromagnet 53a from the plurality of electromagnets 53a, 53b results in a magnetic force acting on a portion 20, if the portion 20 floats in the vicinity of the position below the electromagnet 53a, 53b at the surface of the liquid contained in the reservoir 30. Active electromagnets 53a, through which an electric current is flowing, so that a magnetic field is provided by the active electromagnets 53a, are depicted by solid lines. Inactive electromagnets 53b, through which no electric current is flowing, so that no magnetic field is provided by the inactive electromagnets 53b, are depicted by dashed lines.

In FIG. 9A, a magnetic field is produced by the active electromagnets 53a positioned above the outer rim of the reservoir 30. These active electromagnets 53a are activated by electric currents flowing through the active electromagnets 53a. The active electromagnets 53a form a rectangular shape, which surrounds a first area at the surface of the liquid contained in the reservoir 30. Thereby, a subset of portions 20 of a rigid body 1 in the vicinity of the active electromagnets 53a is moved to positions below the active electromagnets 53a by the action of the magnetic forces provided by the magnetic fields provided by the active electromagnets 53a.

In FIG. 9B, a magnetic field is produced by the active electromagnets 53a positioned adjacent to the active electromagnets 53a shown in FIG. 9A, and closer to the center of the reservoir 30. The active electromagnets 53a form a rectangular shape, which surrounds a second area at the surface of the liquid contained in the reservoir 30, wherein the second area is smaller than the first area. Thereby, the portions 20 positioned outside of the second area have been moved to positions in the vicinity of the second area and the density of portions 20 in the vicinity of the second area has been increased compared to the density of portions 20 in the vicinity of the first area in FIG. 9A.

In FIG. 9C, a magnetic field is produced by the active electromagnets 53a positioned adjacent to the active electromagnets 53a shown in FIG. 9B, and closer to the center of the reservoir 30. The active electromagnets 53a form a rectangular shape, which surrounds a third area at the surface of the liquid contained in the reservoir 30, wherein the third area is smaller than the first area. Thereby, the portions 20 of a rigid body 1 positioned outside of the third area have been moved to positions in the vicinity of the third area and the density of portions 20 of a rigid body 1 in the vicinity of the third area has been increased compared to the density of portions 20 in the vicinity of the second area in FIG. 9B.

In this way, the density of portions 20 can be increased and portions 20 can be moved to specific positions at the surface of the liquid contained in the reservoir 30, for instance above a support structure, such as an imaging grid or a silicon wafer. Subsequently, the distance of the support structure to the surface of the liquid can be reduced, for example by removing liquid from the reservoir 30, so that the portions 20 are carried by the support structure. The support structure can then be removed, dried, and the portions 20 can be subjected to microscopic imaging.

Figure 10:
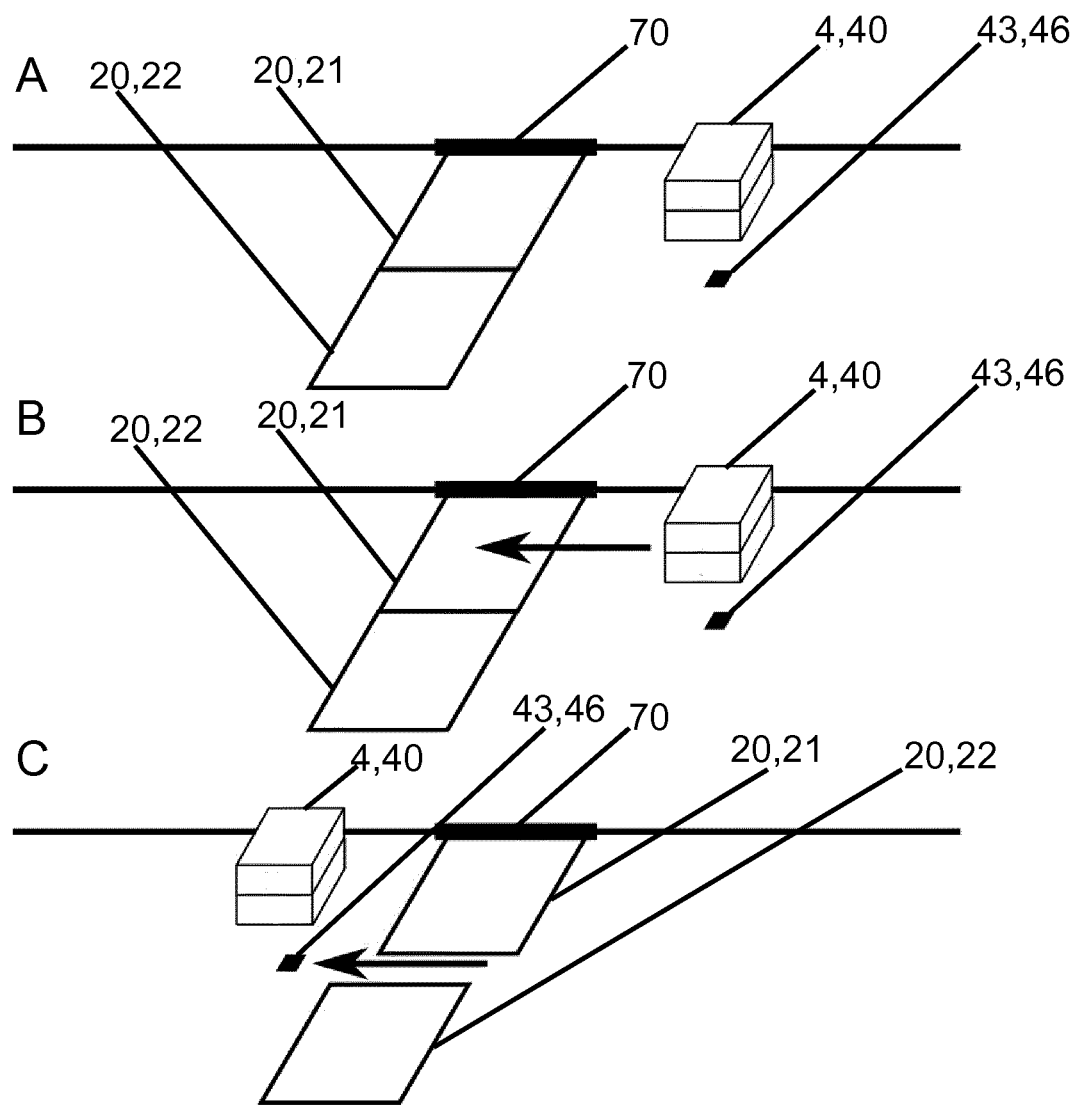
FIG. 10 shows an edge of a diamond knife, a permanent magnet, a floatable knife, a first portion of a rigid body, and a second portion of a rigid body.

FIG. 10 shows a permanent magnet 40, a knife edge 70 of a diamond knife, a first portion 21 of a rigid body 1, a second portion 22 of a rigid body 1, and a floatable knife 46 comprising magnetic or magnetizable material, wherein the first portion 21, the second portion 22, and the floatable knife 46 float at the surface of a liquid contained in a reservoir 30 and wherein the permanent magnet 40 is positioned above the surface of the liquid, so that the magnetic field provided by the permanent magnet 40 results in a magnetic force acting on the floatable knife 46 at the surface of the liquid.

In FIG. 10A, a first edge of the first portion 21 of a rigid body 1 is shown adhering to the knife edge 70 of the diamond knife, which represents a typical situation directly after the first portion 21 has been cut from a rigid body 1 by the diamond knife. A first edge of the second portion 22 of a rigid body 1 is shown adhering to a second edge of the first portion 21. This situation typically occurs if the second portion 22 has been cut from a rigid body 1 directly prior to the first portion 21.

FIG. 10B shows a movement of the permanent magnet 40 towards a position above the first portion 21 of a rigid body 1 and the second portion 22 of a rigid body 1. The floatable knife 46 is moved towards the first portion 21 and the second portion 22 at the surface of the liquid by the effect of the magnetic force provided by the magnetic field provided by the permanent magnet 40.

FIG. 10O shows a movement of the permanent magnet 40 above the second edge of the first portion 21 of a rigid body 1 and the first edge of the second portion 22 of a rigid body 1 resulting in a movement of the floatable knife 46 at the surface of the liquid, wherein the floatable knife 46 separates the second edge of the first portion 21 from the first edge of the second portion 22.

In this manner, the first portion 21 is separated from the second portion 22, so that the second portion 22 may be moved to a specific position at the surface of the liquid individually or so that the second portion 22 may be positioned on a support structure and removed from the reservoir 30 to perform microscopic imaging.

Figure 11:
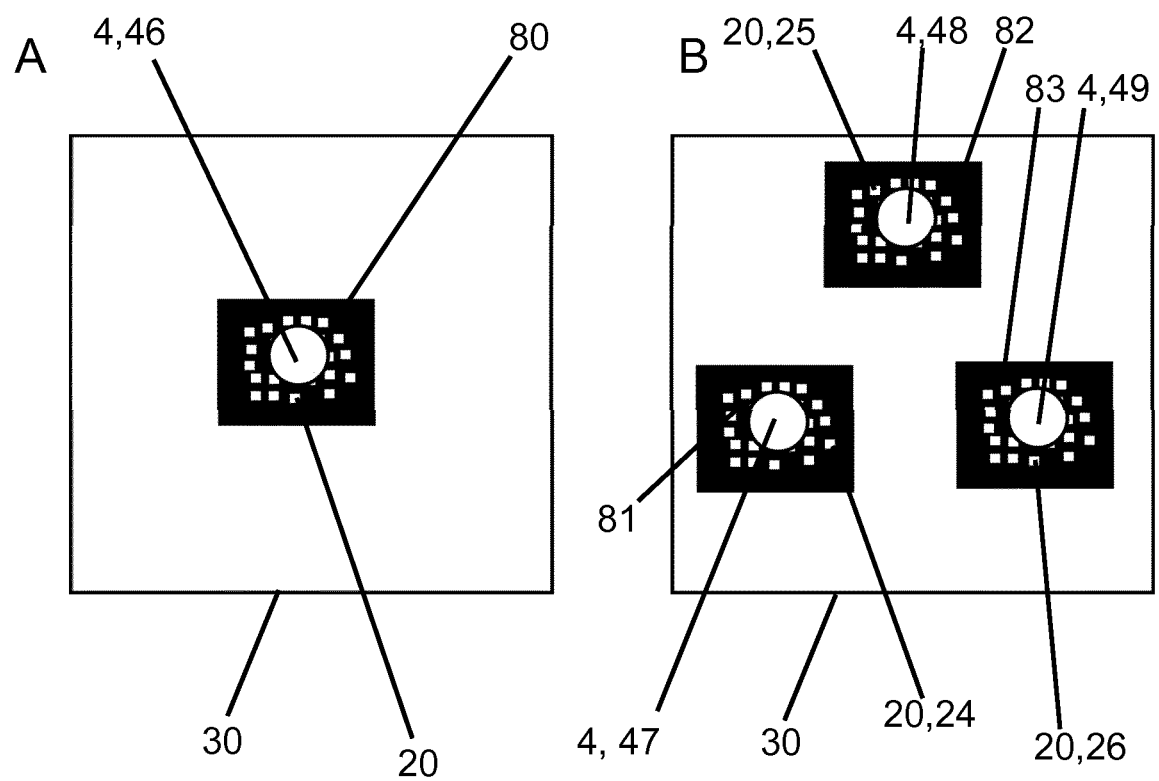
FIG. 11 shows a top view of a reservoir, a first magnetic device, a second magnetic device, a third magnetic device, a plurality of portions of a rigid body, a first support structure, a second support structure, and a third support structure.

Specifically, FIG. 11A shows a top view of a reservoir 30, a support structure 80, wherein the support structure 80 is positioned in the reservoir 30, and a plurality of portions 20 of a rigid body 1 comprising magnetic or magnetizable material, wherein the plurality of portions 20 are floating at the surface of the liquid contained in the reservoir 30, and a magnetic device 4 providing a magnetic field, particularly a permanent magnet or an electromagnet. The plurality of portions 20 are positioned at the surface of the liquid above the support structure 80. The magnetic device 4 is positioned above the surface of the liquid and above the support structure 80 at a position, where the magnetic field provided by the magnetic device 4 provides a magnetic force acting on the plurality of portions 20, so that the portions 20 are contained at a position above the support structure 80.

FIG. 11B shows a top view of a reservoir 30, a first support structure 81, a second support structure 82, and a third support structure 83, wherein the first support structure 81, the second support structure 82, and the third support structure 83 are positioned in the reservoir 30. Further, FIG. 11B shows a first plurality of portions 24 of a rigid body 1, a second plurality of portions 25 of a rigid body 1 and a third plurality of portions 26 of a rigid body 1, wherein the first plurality of portions 24, the second plurality of portions, and the third plurality of portions 26 comprise magnetic or magnetizable material and are floating at the surface of the liquid contained in the reservoir 30. FIG. 11B further shows a first magnetic device 47, a second magnetic device 48, and a third magnetic device 49, wherein the first magnetic device 47, the second magnetic device 48, and the third magnetic device 49 provide a magnetic field and particularly comprise a permanent magnet or an electromagnet. The first plurality of portions 24 is positioned at the surface of the liquid above the first support structure 81, the second plurality of portions 25 is positioned at the surface of the liquid above the second support structure 82, and the third plurality of portions 26 is positioned at the surface of the liquid above the third support structure 83. The first magnetic device 47 is positioned above the surface of the liquid and above the first support structure 81 at a position, where the magnetic field provided by the first magnetic device 47 provides a magnetic force acting on the first plurality of portions 24, so that the first plurality of portions 24 is contained at a position above the first support structure 81. The second magnetic device 48 is positioned above the surface of the liquid and above the second support structure 82 at a position, where the magnetic field provided by the second magnetic device 48 provides a magnetic force acting on the second plurality of portions 24, so that the second plurality of portions 25 is contained at a position above the second support structure 82. The third magnetic device 49 is positioned above the surface of the liquid and above the third support structure 83 at a position, where the magnetic field provided by the third magnetic device 49 provides a magnetic force acting on the third plurality of portions 26, so that the third plurality of portions 26 is contained at a position above the third support structure 83.

In this manner, groups of portions can be sorted to specific support structures and kept above the supports structures by applying a magnetic force. The liquid contained in the reservoir 30 can be subsequently removed or the support structures can be removed from the water, which results in the portions being carried by the support structures. After drying the portions carried by the support structures can be subjected to microscopy.

In the arrangement shown in FIG. 11B, different groups of portions 20 of a rigid body 1 are assigned to specific support structures. For example, every second portion starting with the first, the third, and the fifth portion could be assigned to a first support structure, and every second portion 20 starting with the second, the fourth, and the sixth portion 20 could be assigned to a second support structure.

Alternatively, every third portion 20 starting with the first, fourth, and seventh portion 20 cut from a rigid body 1 could be assigned to a first support structure, every third portion 20 starting with the second, the fifth, and the eighth portion 20 could be assigned to a second support structure, and every third portion 20 starting with the third, the sixth, and the ninth portion 20 could be assigned to a third support structure.

By manipulating portions 20 using a magnetic force, portions 20 from a cutting session could be sorted into different groups of portions 20 on different support structures, which could then be subjected to different treatments, for instance staining with different colored dyes, fluorescent dyes or other staining agents, particularly staining agents used for contrast enhancement in electron microscopy.

Figure 12:
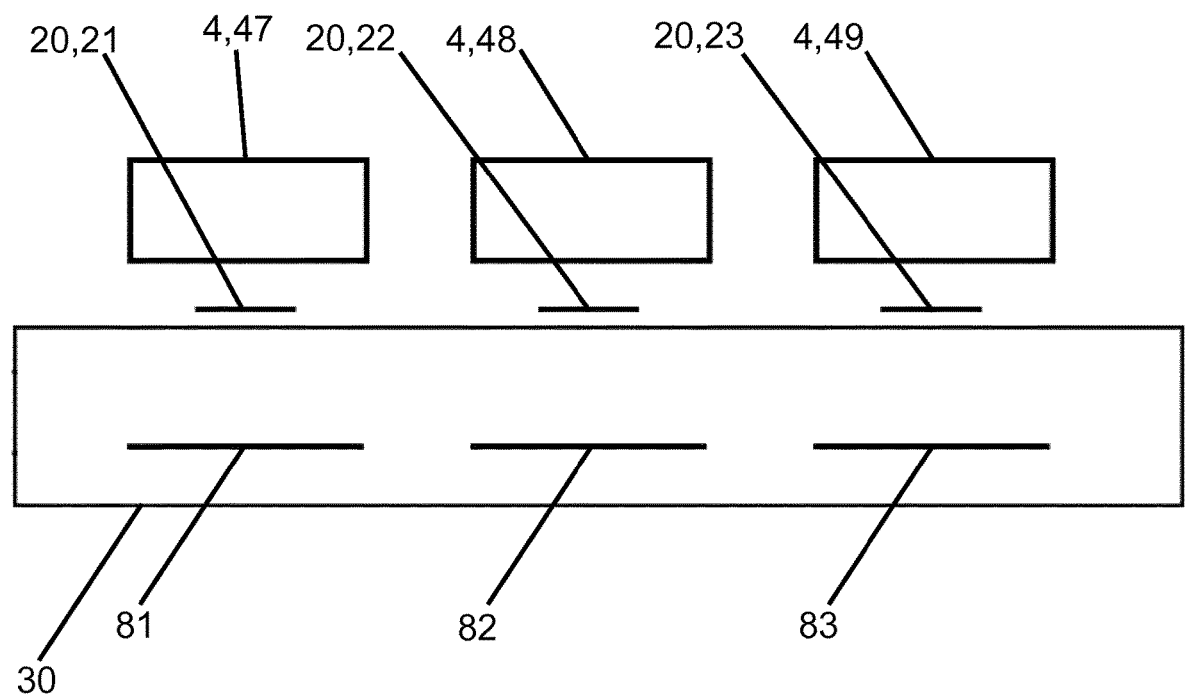
FIG. 12 shows a side view of a reservoir, a first magnetic device, a second magnetic device, a third magnetic device, a first portion of a rigid body, a second portion of a rigid body, a third portion of a rigid body, a first support structure, a second support structure, and a third support structure.

FIG. 12 shows a cross section of a reservoir 30 containing a liquid, a first portion 21 of a rigid body 1 comprising a magnetic or magnetizable material, wherein the first portion 21 is floating at the surface of the liquid at a first position, a first magnetic device 47 providing a first magnetic field, wherein the first magnetic device 47 is positioned above the first position, so that the first magnetic field provides a magnetic force acting on the first portion 21, and a first support structure 81, wherein the first support structure 81 is positioned in the reservoir 30 below the first position, so that the first portion 21 may be carried by the first support structure 81 if the surface of the liquid is lowered or if the first support structure 81 is raised.

Furthermore, FIG. 12 shows a second portion 22 of a rigid body 1 comprising a magnetic or magnetizable material, wherein the second portion 22 of a rigid body 1 is floating at the surface of the liquid at a second position, a second magnetic device 48 providing a second magnetic field, wherein the second magnetic device 48 is positioned above the second position, so that the second magnetic field provides a magnetic force acting on the second portion 22, and a second support structure 82, wherein the second support structure 82 is positioned in the reservoir 30 below the second position, so that the second portion 22 may be carried by the second support structure 82 if the surface of the liquid is lowered or if the second support structure 82 is raised.

Furthermore, FIG. 12 shows a third portion 23 of a rigid body 1 comprising a magnetic or magnetizable material, wherein the third portion 23 is floating at the surface of the liquid at a third position, a third magnetic device 49 providing a third magnetic field, wherein the third magnetic device 49 is positioned above the third position, so that the third magnetic field provides a magnetic force acting on the third portion 23, and a third support structure 83, wherein the third support structure 83 is positioned in the reservoir 30 below the third position, so that the third portion 23 may be carried by the third support structure 83 if the surface of the liquid is lowered or if the third support structure 83 is raised.

Figure 13:
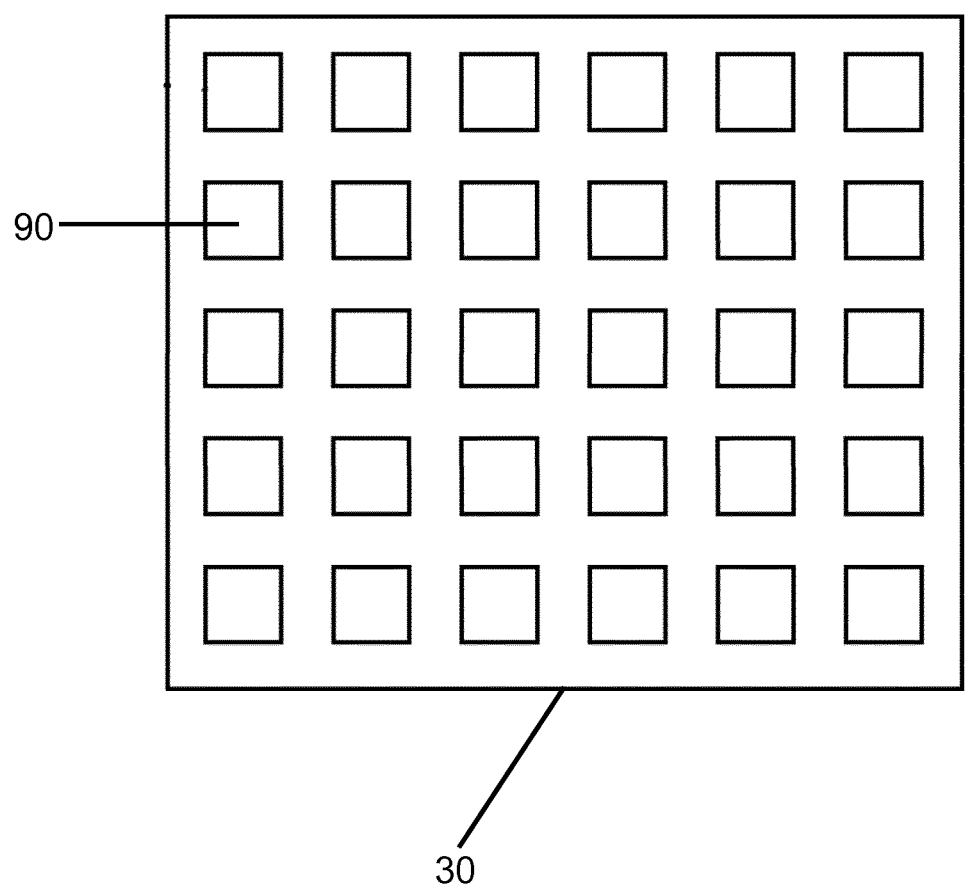
FIG. 13 shows a top view of a reservoir and a plurality of membranes.

FIG. 13 shows a top view of a reservoir 30 containing a liquid, and a plurality of membranes 90, wherein the plurality of membranes 90 is positioned in the reservoir 30, so that portions 20 of a rigid body 1 comprising a magnetic or magnetizable material can be moved above the membranes by applying a magnetic force. After lowering the level of the liquid, the membranes 90 carrying portions 20 can be removed and the portions 20 can be imaged using transmission electron microscopy, scanning transmission electron microscopy, or light microscopy.

Specifically, FIG. 14A-F show a reservoir 30 containing a liquid, a first plurality of portions 24 of a rigid body 1 comprising a magnetic or magnetizable material, wherein the first plurality of portions 24 is floating at the surface of the liquid in the vicinity of a first position at the surface of the liquid and a second plurality of portions 25 of a rigid body 1 comprising a magnetic or magnetizable material, wherein the second plurality of portions 25 is floating at the surface of the liquid in the vicinity of a second position at the surface of the liquid.

FIG. 14A-F further shows a first support structure 81, wherein the first support structure 81 is positioned in the reservoir 30 below the first position, and a second support structure 82, wherein the second support structure 82 is positioned in the reservoir 30 below the second position.

FIG. 14A-F further show a first magnetic device 47 providing or adapted to provide a first magnetic field, wherein the first magnetic device 47 is positioned above the first position, so that the first magnetic field may provide a magnetic force acting on portions 20 of a rigid body 1 of the first plurality of portions 24 of a rigid body 1.

FIG. 14A-F further show a second magnetic device 48 providing or adapted to provide a second magnetic field, wherein the second magnetic device is positioned above the second position, so that the second magnetic field may provide a magnetic force acting on portions 20 of a rigid body 1 of the second plurality of portions 25.

FIG. 14A-F further show a third magnetic device 49 providing or adapted to provide a third magnetic field, wherein the third magnetic device 49 is positioned above the surface of the liquid, so that the third magnetic field may provide a magnetic force acting on portions 20 of a rigid body 1 comprising a magnetic or magnetizable material floating at the surface of the liquid below the third magnetic device 49, and wherein the third magnetic device 49 is movable above the surface of the liquid, and wherein the third magnetic field provided by the third magnetic device 49 is weaker than the first magnetic field provided by the first magnetic device 47, and wherein the third magnetic field provided by the third magnetic device 49 is weaker than the second magnetic field provided by the second magnetic device 48.

FIG. 14A-F further show a knife edge 70 of a diamond knife, wherein the knife edge 70 is positioned near the surface of the liquid at the boundary of the reservoir 30, a first portion 21 of a rigid body 1 comprising a magnetic or magnetizable material, wherein the first portion 21 is floating at the surface of the liquid. Furthermore, FIG. 14D-F show a second portion 22 of a rigid body 1 comprising a magnetic or magnetizable material, wherein the second portion 22 is floating at the surface of the liquid.

FIG. 14A depicts a situation, in which the first portion 21 of a rigid body 1 has just been cut from a rigid body 1 by the diamond knife and has just been removed from the knife edge 70 to float at the surface of the liquid. For example, a portion 20 adhering to the knife edge 70 could be removed from the knife edge 70 using a magnetic force provided by a magnetic field provided by a magnetic device, particularly the third magnetic device 49 shown. In FIG. 14A the third magnetic device 49 is shown positioned above the first portion 21, so that the magnetic field provided by the third magnetic device 49 provides a magnetic force acting on the first portion 21.

FIG. 14B shows a situation, in which the third magnetic device 49 has been moved above the surface of the liquid to a position above the first position at the surface of the liquid. By the magnetic force provided by the magnetic field provided by the third magnetic device 49, the first portion 21 of a rigid body 1 has been moved at the surface of the liquid to the vicinity of the first position, close to the first plurality of portions 24 above the first support structure 81.

FIG. 14C shows a situation, in which the third magnetic device 49 has been moved back to a position close to the knife edge 70 of the diamond knife. The first portion 21 of a rigid body 1 has not been moved back by the magnetic force provided by the magnetic field provided by the third magnetic device 49, but remains floating in the vicinity of the first position due to the stronger magnetic force provided by the first magnetic field provided by the first magnetic device 47.

FIG. 14D shows a situation, in which the second portion 22 of a rigid body 1 has just been cut from a rigid body 1 by the diamond knife and has just been removed from the knife edge 70 to float at the surface of the liquid. For example, a portion 20 adhering to the knife edge 70 could be removed from the knife edge 70 using a magnetic force provided by a magnetic field provided by a magnetic device, particularly the third magnetic device 49 shown. In FIG. 14D the third magnetic device 49 is shown positioned above the second portion 22, so that the magnetic field provided by the third magnetic device 49 provides a magnetic force acting on the second portion 22.

FIG. 14E shows a situation, in which the third magnetic device 49 has been moved above the surface of the liquid to a position above the second position at the surface of the liquid. By the magnetic force provided by the magnetic field provided by the third magnetic device 49, the first portion 21 of a rigid body 1 has been moved at the surface of the liquid to the vicinity of the second position, close to the second plurality of portions 25 of a rigid body 1 above the second support structure 82.

FIG. 14F shows a situation, in which the third magnetic device has been moved back to a position close to the knife edge 70 of the diamond knife to receive a further portion 20 of a rigid body 1. The second portion 22 has not been moved back by the magnetic force provided by the magnetic field provided by the third magnetic device, but remains floating in the vicinity of the second position due to the stronger magnetic force provided by the second magnetic field provided by the second magnetic device 48.

In the sequence of events shown by FIG. 14A-F, the first portion 21 of a rigid body 1 has been sorted to the first plurality of portions 24 of a rigid body 1 to be carried by the first support structure 81 and the second portion 22 of a rigid body 1 has been sorted to a second plurality of portions 25 of a rigid body 1 to be carried by the second support structure 82. After removal of the liquid, the first plurality of portions 24 on the first support structure 81 and the second plurality of portions 25 on the second support structure 82 can be optionally subjected to separate staining procedures and subsequently the portions 20 can be separately imaged by microscopy.

Figure 16:
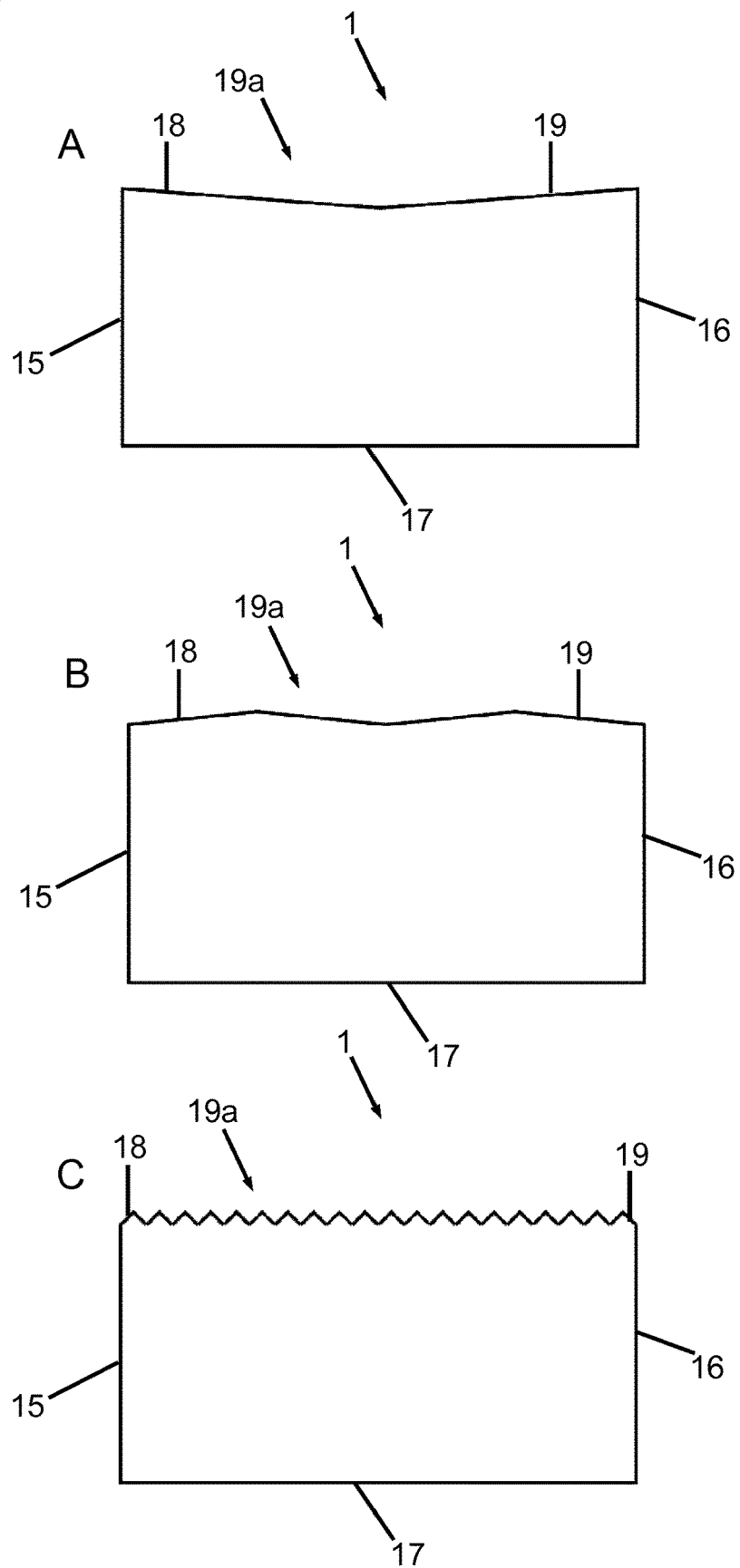
FIG. 16 shows cross-sections of rigid bodies.

An example for a procedure of producing a series of portions 20 of a rigid body 1 using the present invention might comprise the following steps: Ultrathin sections are cut from a rigid body 1 comprising a magnetic or magnetizable material (examples shown in FIGS. 1, 2, and 4) with a conventional ultramicrotome without interruption using a diamond knife. The shape of the rigid body 1 is designed so that adhesion of the portions 20 to each other is minimized (examples shown in FIGS. 3, 4, and 16), leading to isolated single sections moving independently from each other at the liquid surface.

The ultramicrotome is stopped after the desired number of portions 20 has been produced. For example, portions 20 adhering to the knife-edge of the diamond knife may be detached from the edge of the cutting device by applying a magnetic force to the portion 20. Chains of portions 20 adhering to each other may also be detached from each other using a magnetic force acting on the portions 20. Alternatively, a floatable knife (for example as shown in FIG. 10) may be used to separate portions 20 adhering to each other.

Magnetic forces may then be applied to the portions 20, such that they remain at a certain distance from the borders of the reservoir or that they are moved at the surface of the liquid contained in the reservoir. Applying the magnetic forces may be performed for example by using one or several permanent magnets mechanically connected to a movable manipulator (example shown in FIG. 5), permanent magnets mechanically connected to actuators (example shown in FIG. 7), magnetic barriers (example shown in FIG. 8), or an array of electromagnets positioned above the reservoir (FIGS. 6 and 9). Individual electromagnets from the array of electromagnets may be activated by providing an electric current flowing through the electromagnets, which can optionally be controlled by a control device.

Figure 14:
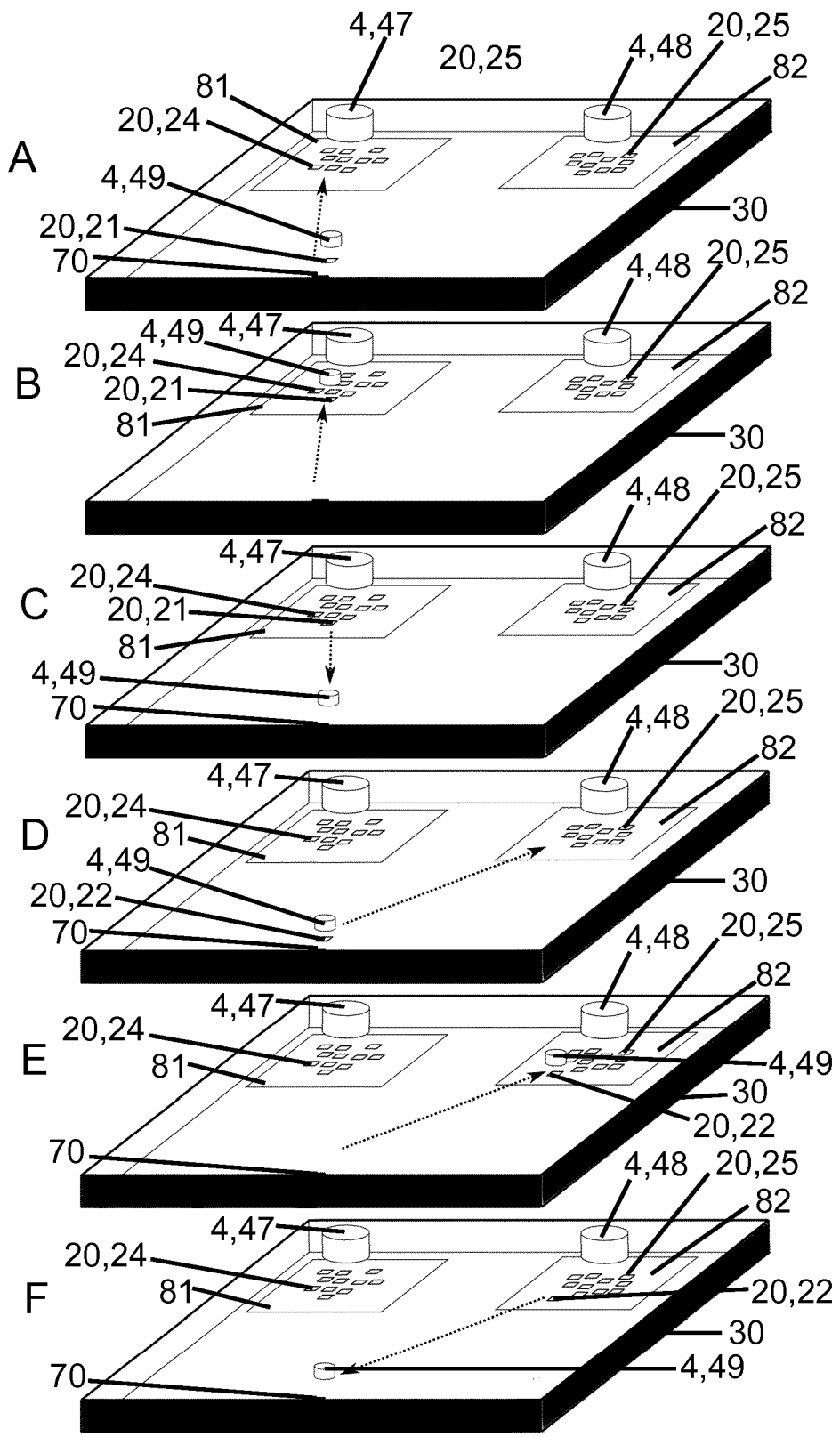
FIG. 14 shows a reservoir, an edge of a diamond knife, a first magnetic device, a second magnetic device, a third magnetic device, a first portion of a rigid body, a second portion of a rigid body, a first plurality of portions of a rigid body, a second plurality of portions of a rigid body, a first support structure, and a second support structure.

Particularly, the portions 20 may be moved and sorted to positions above one or several support structures, particularly imaging grids or silicon wafers that had been previously inserted into the reservoir (example shown in FIG. 14).

The collecting substrates and the surface of the liquid are then brought together slowly, which results in the portions 20 touching the support structures gently to minimize damage to the portions. This may be achieved by lowering the level of the liquid in the reservoir or by lifting the substrate. Particularly, the liquid contained in the reservoir may be removed using a syringe pump.

Water is then evaporated from the surface of the support structures, which may be accelerated by a heating system.

The portions 20 carried by the support structures may then be stored, or further processed, particularly stained, and analyzed by microscopy, particularly electron microscopy or light microscopy.

Microscopic images may be generated, particularly using a detector and/or a digital camera. From the generated microscopic images of each portion 20, the original order in which the portions 20 were cut from the rigid body 1, which corresponds to the position of the section in the tissue, may be retrieved using a sorting algorithm. By this algorithm, data sets are first generated from each image. Features are then extracted from the data sets. Using these features, a similarity value or a dissimilarity value between each pair of portions 20 is calculated. The sum of the consecutive similarity values or dissimilarity values is then maximized or minimized by reordering the sections.

Figure 15:
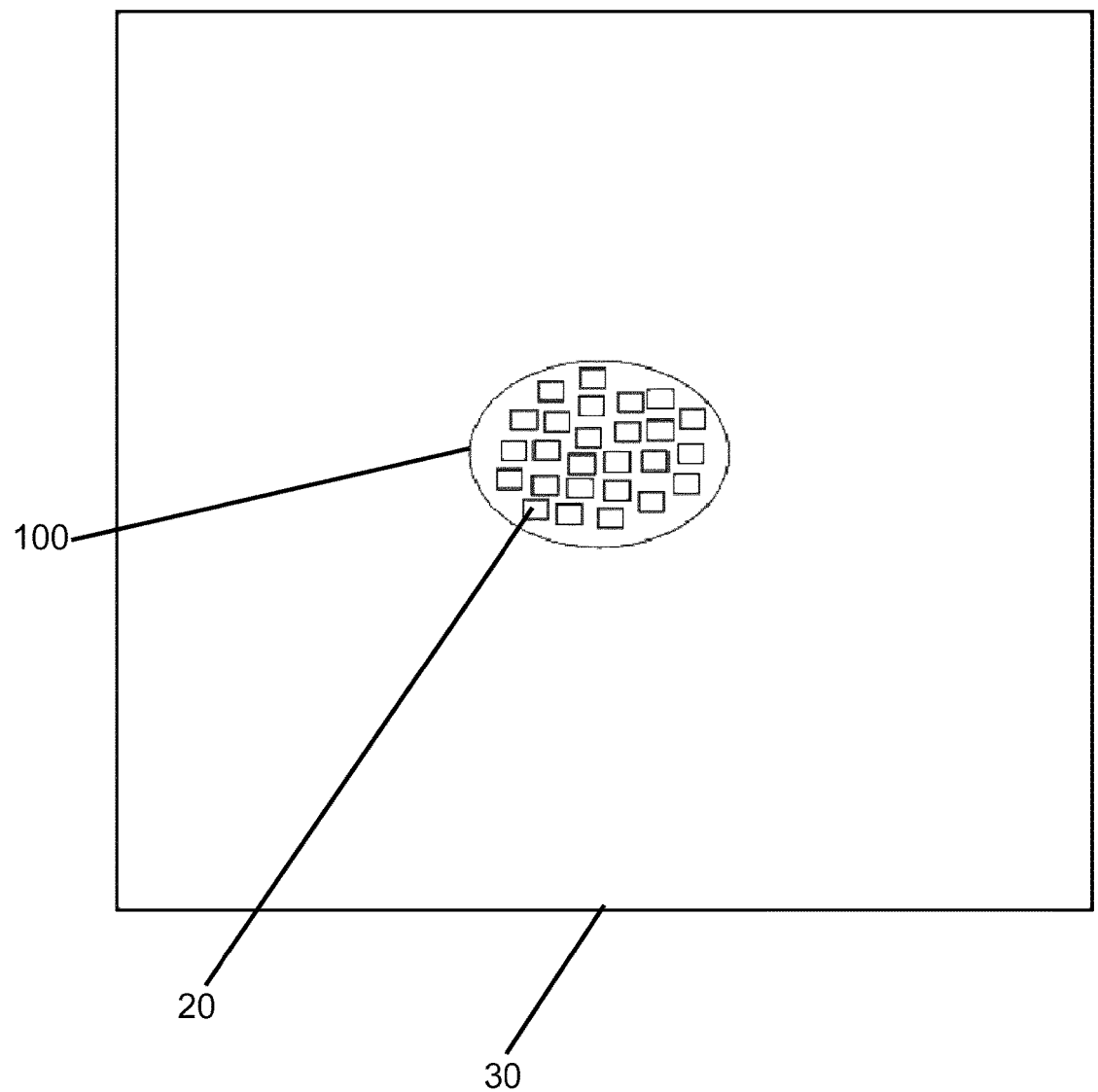
FIG. 15 shows a reservoir, a loop, and a plurality of portions of a rigid body.

FIG. 15 shows a loop 100, particularly a wire loop, which is positioned at the surface of a liquid contained in a reservoir 30 and encircles a plurality of portions 20 of a rigid body 1. The loop 100 is movable at the surface of the liquid, such that the plurality of portions 20 can be moved by means of the loop 100, and/or can be contained at a position at the surface of the liquid.

In particular, the loop 100 may exert a mechanical force on the portions 20.

According to a first alternative, the loop 100 comprises a magnetic material, such that a magnetic field is provided by the loop, which particularly results in a magnetic force acting on the portions 20.

According to a second alternative, the loop 100 comprises magnetizable material, particularly such that the loop 100 is movable at the surface of the liquid by means of a magnetic device, wherein the loop 100 is able to exert a mechanical force on the portions 20.

FIG. 16A shows a cross-section of a rigid body 1 having a first edge 15, a second edge 16, and a third edge 17, which directly connects the first edge 15 and the second edge 16. Therein, the first edge 15 and the third edge 17, and the second edge 16 and the third edge 17 form an angle of 90°.

The cross-section further comprises a plurality of edges 19a forming a zig-zag line, wherein in this example the plurality of edges 19a is composed of a fourth edge 18, and a fifth edge 19, wherein the fourth edge 18 is directly connected to the first edge 15, and wherein the fifth edge 19 is directly connected to the second edge 16. In this example, the fourth edge 18 and the fifth edge 19 are directly connected.

The fourth edge 18 and the fifth edge 19 are arranged such that the fourth edge 18 forms an angle of less than 90° with the first edge 15, and the fifth edge 19 forms an angle of less than 90° with the second edge 16, resulting in a zig-zag line.

FIG. 16B shows a cross-section of a rigid body 1 having a first edge 15, a second edge 16, and a third edge 17, which directly connects the first edge 15 and the second edge 16. Therein, the first edge 15 and the third edge 17, and the second edge 16 and the third edge 17 form an angle of 90°.

The cross-section further comprises a plurality of edges 19a forming a zig-zag line, wherein in this example the plurality of edges 19a is composed of a fourth edge 18, a fifth edge 19, and two further edges, wherein the fourth edge 18 is directly connected to the first edge 15, and wherein the fifth edge 19 is directly connected to the second edge 16. In this example, the fourth edge 18 and the fifth edge 19 are connected by the two further edges.

The fourth edge 18 and the fifth edge 19 are arranged such that the fourth edge 18 forms an angle between 90° and 270° with the first edge 15, and the fifth edge 19 forms an angle between 90° and 270° with the second edge 16. Furthermore, the two further edges are arranged at an angle with respect to their neighboring edges, such that a zig-zag line is formed by the plurality of edges 19a. FIG. 16C shows a cross-section of a rigid body 1 having a first edge 15, a second edge 16, and a third edge 17, which directly connects the first edge 15 and the second edge 16. Therein, the first edge 15 and the third edge 17, and the second edge 16 and the third edge 17 form an angle of 90°.

The cross-section further comprises a plurality of edges 19a forming a zig-zag line, wherein in this example the plurality of edges 19a is composed of a fourth edge 18, a fifth edge 19, and a plurality of further edges, wherein the fourth edge 18 is directly connected to the first edge 15, and wherein the fifth edge 19 is directly connected to the second edge 16. In this example, the fourth edge 18 and the fifth edge 19 are connected by the plurality of further edges.

The fourth edge 18 and the fifth edge 19 are arranged such that the fourth edge 18 forms an angle between 90° and 270° with the first edge 15, and the fifth edge 19 forms an angle between 90° and 270° with the second edge. Furthermore, the edges comprised in the plurality of further edges are arranged at an angle with respect to their neighboring edges, such that a zig-zag line is formed by the plurality of edges 19a.

Figure 17:
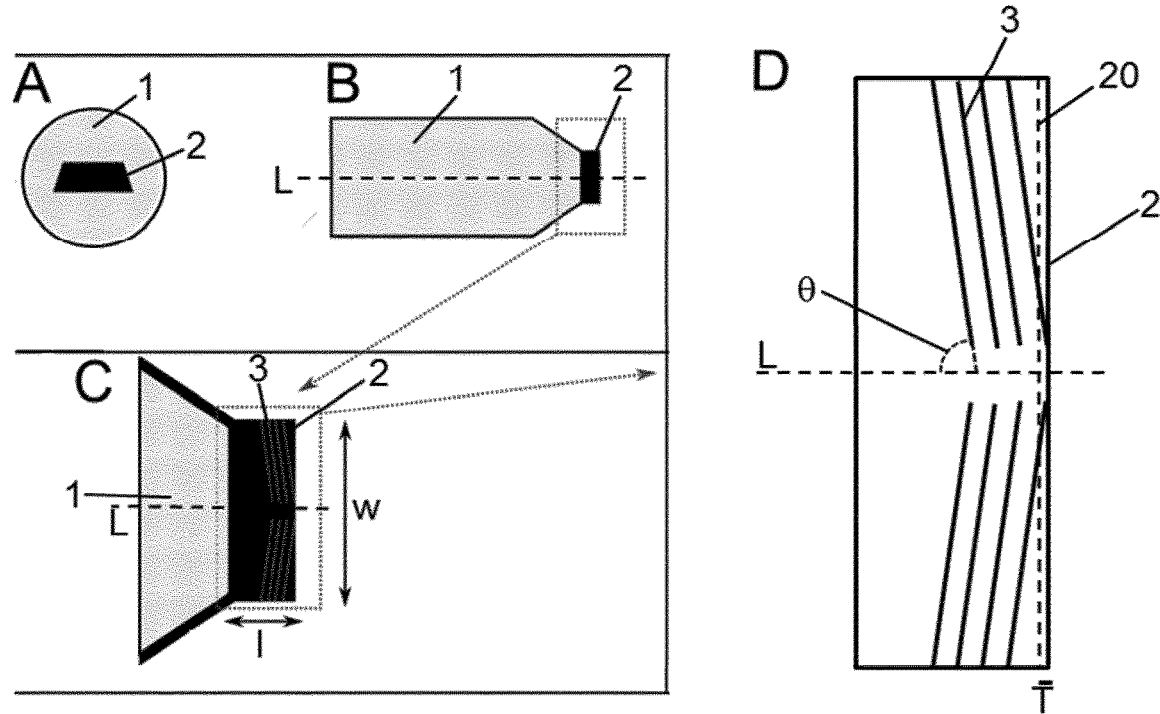
FIG. 17 shows schematic representations of a rigid body comprising markings for order determination of the portions cut from the rigid body.

FIG. 17 shows schematic representations of a cylindrical rigid body 1 extended along a longitudinal axis L, wherein the rigid body 1 has a conical end comprising a front part 2. The front part 2 is adapted such that portions 20 of the rigid body 1 can be cut from the front part 2. The front part 2 comprises markings 3 for order determination of the portions 20 cut from the rigid body 1. For example, the markings 3 may be recesses, particularly applied to the rigid body 1 by means of a laser beam.

FIG. 17A is a front view of the rigid body 1, FIG. 17B is a side view of the rigid body 1, and FIG. 17C is an enlarged side view of the front part 2.

As shown in FIG. 17C, the front part 2 has a length l extending along the longitudinal axis L and a width w perpendicular to the longitudinal axis L.

FIG. 17D shows a further enlarged view of the front section comprising the markings 3. The markings 3 consist of a plurality of lines on the side of the front part 2. The side of the front part 2 carrying the markings 3 comprises a first partial area (above the longitudinal axis L in FIG. 17D) and a second partial area (below the longitudinal axis L in FIG. 17D). The first partial area comprises a first series of markings 3 in the form of parallel lines and the second partial area comprises a second series of markings 3 in the form of parallel lines, wherein the lines of the first series of lines are non-parallel with respect to the second series of lines. The lines are arranged at an angle θ with respect to the longitudinal axis L. The lines of the respective series are arranged at equal distances from each other.

Furthermore, FIG. 17D depicts a portion 20 having a thickness T, wherein the portion 20 is cut or has been cut from the front part 2 of the rigid body 1.

Figure 18:
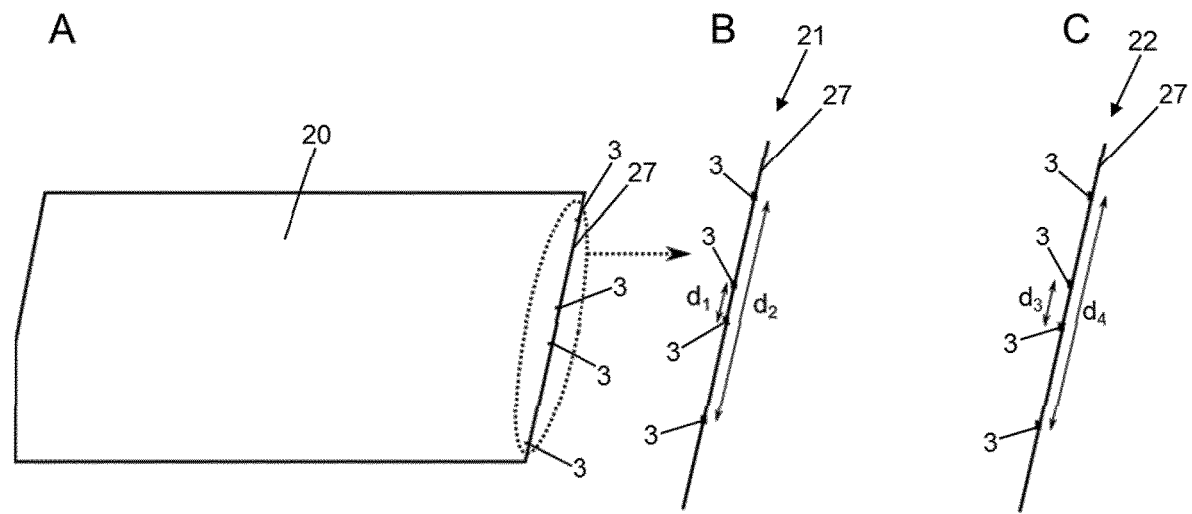
FIG. 18 shows schematic representations of portions of a rigid body comprising markings for order determination.

FIG. 18 shows schematic representations of portions 20 of a rigid body 1 comprising markings 3 for order determination.

FIG. 18A shows a top view of a portion 20 of a rigid body 1, particularly cut from a rigid body 1 as depicted in FIG. 17D. The portion 20 comprises a portion edge 27, which corresponds to the side of the rigid body 1 shown in FIG. 17D carrying the markings 3. The markings 3 on the portion edge 27 correspond to narrow sections (having the thickness T of the respective portion 20) of the lines on the front part 2 of the rigid body 1 (see FIG. 17D). In particular, the markings 3 on the portion edge 27 resulting from the linear-shaped markings 3 on the front part 2 of the rigid body 1 (see FIG. 17D) have the form of dots.

FIG. 18 B shows a portion edge 27 of a first portion 21, and FIG. 18C shows a portion edge 27 of a second portion 22, wherein the second portion 22 has been cut from a rigid block 1 (such as the one shown in FIG. 17D) subsequently to the first portion 21. The portion edges 27 each comprise four markings 3, wherein the inner markings of the first portion 21 are arranged at a first distance $d_1$ from each other, the outer markings of the first portion 21 are arranged at a second distance $d_2$ from each other, the inner markings of the second portion 22 are arranged at a third distance $d_3$ from each other, and the outer markings of the second portion 22 are arranged at a fourth distance $d_4$ from each other.

As is apparent from FIG. 17D and FIG. 18, the position of the markings 3 on the portion edge 27, and therefore also the distances $d_1$, $d_2$, $d_3$, and $d_4$ depend on the prior position of the respective portion 20 in the rigid body 1, from which the portion 20 has been cut.

Thus, in the two subsequently cut portions 21,22 shown in FIGS. 18B and 18C the distance $d_1$ of the markings 3 on the first portion 21 differs from the distance $d_3$ of the markings 3 on the second portion 22, and the distance $d_2$ of the markings 3 on the first portion 21 differs from the distance $d_4$ of the markings 3 on the second portion 22, wherein particularly the third distance $d_3$ is larger than the first distance $d_1$, and the fourth distance $d_4$ is larger than the second distance $d_2$. In particular, the difference between $d_3$ and $d_1$ equals 2T*tan θ, wherein T is the thickness of the first portion 21 and/or the second portion 22, and wherein θ is the angle between the longitudinal axis L and the line markings 3 on the front part 2 of the rigid body 1 (see FIG. 17D). From these differences of the distance values $d_1$, $d_2$, $d_3$, $d_4$, the order, in which the portions 20,21,22, were cut from the rigid body 1 can be determined.

For example, the thickness T may be 50 nm, and the angle may be 80°, wherein the distance (d3−d1)+(d4−d2) between two consecutive sections is 1134 nm.

These values are measurable by light microscopy or electron microscopy, such that the order in which portions 20 have been cut from a rigid body 1 can be determined.

| List of reference signs | |
|---|---|
| Rigid body | 1 |
| Front part | 2 |
| Marking | 3 |
| First layer | 11 |
| Second layer | 12 |
| Third layer | 13 |
| Magnetic or magnetizable material | 14 |
| First edge | 15 |
| Second edge | 16 |
| Third edge | 17 |
| Fourth edge | 18 |
| Fifth edge | 19 |
| Plurality of edges | 19a |
| Portion of a rigid body | 20 |
| First portion of a rigid body | 21 |
| Second portion of a rigid body | 22 |
| Third portion of a rigid body | 23 |
| First plurality of portions of a rigid body | 24 |
| Second plurality of portions of a rigid body | 25 |
| Third plurality of portions of a rigid body | 26 |
| Portion edge | 27 |
| Reservoir | 30 |
| Surface | 31 |
| First position | 32 |

-continued

| List of reference signs | |
|---|---|
| Second position | 33 |
| Magnetic device | 4 |
| Permanent magnet | 40 |
| First permanent magnet | 41 |
| Second permanent magnet | 42 |
| Floatable device | 43 |
| First magnetic barrier | 44 |
| Second magnetic barrier | 45 |
| Floatable knife | 46 |
| First magnetic device | 47 |
| Second magnetic device | 48 |
| Third magnetic device | 49 |
| Electromagnet | 50 |
| First electromagnet | 51 |
| Second electromagnet | 52 |
| Active electromagnet | 53a |
| Inactive electromagnet | 53b |
| Manipulator arm | 60 |
| First actuator | 61 |
| Second actuator | 62 |
| Knife edge | 70 |
| Support structure | 80 |
| First support structure | 81 |
| Second support structure | 82 |
| Third support structure | 83 |
| Membrane | 90 |
| Loop | 100 |
| Longitudinal axis | L |
| Width | W |
| Length | L |
| Angle | θ |
| Thickness | T |
| First distance | $d_1$ |
| Second distance | $d_2$ |
| Third distance | $d_3$ |
| Fourth distance | $d_4$ |

The invention claimed is:

1. Method for manipulating at least one portion of a rigid body,
comprising the steps of:
   i. providing a rigid body comprising ultrathin-sectionable material,
   ii. cutting an ultrathin portion from said rigid body,
   iii. providing said portion at a surface of a liquid,
   iv. providing at least one magnetic device, which produces a magnetic field or which is able to produce a magnetic field, and
   v. using the magnetic field in order to provide a magnetic force, and using the magnetic force to move said portion along a plane which is parallel to the surface of the liquid to a specified position at the surface of the liquid.

2. Method for manipulating at least one portion of a rigid body according to claim 1, wherein said rigid body comprises a biological material.

3. Method for manipulating at least one portion of a rigid body according to claim 1, wherein the portion comprises a magnetic or magnetizable material, and wherein said magnetic field acts on the magnetic or magnetizable material, such that said magnetic force directly acts on the portion.

4. Method for manipulating at least one portion of a rigid body according to claim 1, wherein a floatable device is provided, wherein the floatable device floats at the surface of said liquid, and wherein the floatable device comprises a magnetic or magnetizable material, and a) said magnetic field acts on the floatable device, such that a magnetic force acts on the floatable device, wherein the floatable device is moved by the magnetic force, and wherein the floatable device exerts a mechanical force on at least one portion, such that the portion is moved at the surface of the liquid, or b) said magnetic field provided by the floatable device exerts a magnetic force on at least one portion, such that the portion is moved at the surface of the liquid.

5. Method for manipulating at least one portion of a rigid body according to claim 1, comprising the steps of
moving at least one portion at the surface of said liquid to a position above a support structure by using said magnetic force, and
reducing the distance between the surface of said liquid and the support structure, such that the portion is carried by the support structure.

6. Method for manipulating at least one portion of a rigid body according to claim 1, wherein at least one image is taken of a plurality of portions, and wherein the plurality of portions provided are in an order determined by means of the at least one image.

7. Method for manipulating at least one portion of a rigid body according to claim 6, wherein an optically detectable pattern is introduced into the rigid body, and wherein at least a part of the pattern on a respective portion cut from the rigid body is detected by means of taking said at least one image, and wherein the order, in which the portions have been provided, is determined by means of said part of the pattern.

8. Method for manipulating at least one portion of a rigid body according to claim 6, wherein at least one marker particle is provided in the rigid body, wherein the marker particle can be visualized by an imaging technique electron microscopy, or light microscopy and wherein portions of the rigid body comprise at least one segment of said marker particle, and wherein the order, in which the portions have been provided, is determined by evaluating at least one optically detectable parameter of said segment.

9. Method for manipulating at least one portion of a rigid body according to claim 1, wherein the portions provided are in an order that is determined, and wherein the method further comprises the steps of
taking at least one image of a plurality of portions,
generating a data set for each portion of the at least one image,
comparing each pair of data sets, wherein a distance value is determined for each pair of data sets, and wherein the distance value reflects a similarity or dissimilarity of each pair of data sets,
generating a plurality of orders of the data sets,
determining a sum of distance values of neighboring pairs of data sets of the order,
comparing sums of distance values of the generated orders,
selecting an order having a maximal sum of distance values reflecting the similarity, or having a minimal sum of distance values reflecting the dissimilarity.

10. Computer program comprising a program code for the execution of the steps of the method described in claim 1, when the computer program is loaded or executed on a computer.

* * * * *